US007951402B2

(12) United States Patent
Lanphere et al.

(10) Patent No.: US 7,951,402 B2
(45) Date of Patent: *May 31, 2011

(54) DRUG DELIVERY PARTICLE

(75) Inventors: Janel Lanphere, Hyde Park, MA (US);
Erin McKenna, Boston, MA (US);
Wendy Naimark, Cambridge, MA (US);
Marcia Buiser, Watertown, MA (US);
Stephan Mangin, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/235,978

(22) Filed: Sep. 23, 2008

(65) Prior Publication Data

US 2009/0035352 A1 Feb. 5, 2009

Related U.S. Application Data

(63) Continuation of application No. 10/232,265, filed on Aug. 30, 2002, now Pat. No. 7,462,366.

(51) Int. Cl.
*A61K 9/14* (2006.01)
*A61K 9/50* (2006.01)
(52) U.S. Cl. .................. 424/489; 424/499; 424/501
(58) Field of Classification Search .................. None
See application file for complete search history.

(56) References Cited

U.S. PATENT DOCUMENTS

| | | | |
|---|---|---|---|
| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Moiser |
| 4,515,906 A | 5/1985 | Friesen et al. |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,629,464 A | 12/1986 | Takata et al. |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,695,466 A | 9/1987 | Morishita et al. |
| 4,713,076 A | 12/1987 | Draenert |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |

(Continued)

FOREIGN PATENT DOCUMENTS

AU    A-76186/98    10/1998

(Continued)

OTHER PUBLICATIONS

Kim et al., "Poly (vinyl alcohol) beads with core-shell structure for drug delivery," Cosmetic & Pharmaceutical Applications of Polymers, Plenum Press, NY, pp. 209-214, (1991).
Abbara et al., "Transcervical Expulsion of a Fibroid as a Result of Uterine Artery Embolization for Leiomyomata", *JVIR*, vol. 10, No. 4, pp. 409-411, 1999.
Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.
Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.
Ahuja, A.A., "Platinum Coil Coatings to Increase Thrombogenicity: A Preliminary Study in Rabbits", *AJNR Am. J. Neuroradiol.* 14:794-798; Jul./Aug. 1993.
Antibody Labeling, http://www.altcorp.com/AffinityLabeling/ablaeling.htm, pp. 1-6, May 20, 2003.
Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.

(Continued)

*Primary Examiner* — Elli Peselev
(74) *Attorney, Agent, or Firm* — Fish & Richardson P.C.

(57) ABSTRACT

A drug delivery particle including a reservoir region having primarily large pores and a metering region. The particle can be highly spherical.

25 Claims, 10 Drawing Sheets

U.S. PATENT DOCUMENTS

| | | | |
|---|---|---|---|
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |
| 4,897,255 A | 1/1990 | Fritzberg et al. |
| 4,929,400 A | 5/1990 | Rembaum et al. |
| 4,933,372 A | 6/1990 | Feibush et al. |
| 4,938,967 A | 7/1990 | Newton et al. |
| 4,946,899 A | 8/1990 | Kennedy et al. |
| 4,954,399 A | 9/1990 | Tani et al. |
| 4,981,625 A | 1/1991 | Rhim et al. |
| 4,990,340 A | 2/1991 | Hidaka et al. |
| 4,999,188 A | 3/1991 | Sloldovnik et al. |
| 5,007,940 A | 4/1991 | Berg |
| 5,011,677 A | 4/1991 | Day et al. |
| H915 H | 5/1991 | Gibbs |
| 5,015,423 A | 5/1991 | Eguchi et al. |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,091,205 A | 2/1992 | Fan |
| 5,106,903 A | 4/1992 | Vanderhoff et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A | 3/1993 | Kamiya et al. |
| 5,202,352 A | 4/1993 | Okada et al. |
| 5,216,096 A | 6/1993 | Hattori et al. |
| 5,253,991 A | 10/1993 | Yokota et al. |
| 5,260,002 A | 11/1993 | Wang |
| 5,262,176 A | 11/1993 | Palmacci et al. |
| 5,263,992 A | 11/1993 | Guire |
| 5,288,763 A | 2/1994 | Li et al. |
| 5,292,814 A | 3/1994 | Bayer et al. |
| 5,302,369 A | 4/1994 | Day et al. |
| 5,314,974 A | 5/1994 | Ito et al. |
| 5,316,774 A | 5/1994 | Eury et al. |
| RE34,640 E | 6/1994 | Kennedy et al. |
| 5,320,639 A | 6/1994 | Rudnick |
| 5,328,936 A | 7/1994 | Leifholtz et al. |
| 5,336,263 A | 8/1994 | Ersek et al. |
| 5,344,452 A | 9/1994 | Lemperle |
| 5,344,867 A | 9/1994 | Morgan et al. |
| 5,354,290 A | 10/1994 | Gross |
| 5,369,133 A | 11/1994 | Ihm et al. |
| 5,369,163 A | 11/1994 | Chiou et al. |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,417,982 A | 5/1995 | Modi |
| 5,431,174 A | 7/1995 | Knute |
| 5,435,645 A | 7/1995 | Faccioli et al. |
| 5,443,495 A | 8/1995 | Buscemi et al. |
| 5,456,693 A | 10/1995 | Conston et al. |
| 5,468,801 A | 11/1995 | Antonelli et al. |
| 5,469,854 A | 11/1995 | Unger et al. |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,514,379 A | 5/1996 | Weissleder et al. |
| 5,525,334 A | 6/1996 | Ito et al. |
| 5,534,589 A | 7/1996 | Hager et al. |
| 5,541,031 A | 7/1996 | Yamashita et al. |
| 5,542,935 A | 8/1996 | Unger et al. |
| 5,553,741 A | 9/1996 | Sancoff et al. |
| 5,556,610 A | 9/1996 | Yan et al. |
| 5,558,255 A | 9/1996 | Sancoff et al. |
| 5,558,822 A | 9/1996 | Gitman et al. |
| 5,558,856 A | 9/1996 | Klaveness et al. |
| 5,559,266 A | 9/1996 | Klaveness et al. |
| 5,567,415 A | 10/1996 | Porter |
| 5,569,193 A | 10/1996 | Hofstetter et al. |
| 5,569,449 A | 10/1996 | Klaveness et al. |
| 5,569,468 A | 10/1996 | Modi |
| 5,571,182 A | 11/1996 | Ersek et al. |
| 5,580,575 A | 12/1996 | Unger et al. |
| 5,583,162 A | 12/1996 | Li et al. |
| 5,585,112 A | 12/1996 | Unger et al. |
| 5,595,821 A | 1/1997 | Hager et al. |
| 5,622,657 A | 4/1997 | Takada et al. |
| 5,624,685 A | 4/1997 | Takahashi et al. |
| 5,635,215 A | 6/1997 | Boschetti et al. |
| 5,637,087 A | 6/1997 | O'Neil et al. |
| 5,639,710 A | 6/1997 | Lo et al. |
| 5,648,095 A | 7/1997 | Illum et al. |
| 5,648,100 A | 7/1997 | Boschetti et al. |
| 5,650,116 A | 7/1997 | Thompson |
| 5,651,990 A | 7/1997 | Takada et al. |
| 5,653,922 A | 8/1997 | Li et al. |
| 5,657,756 A | 8/1997 | Vrba et al. |
| 5,681,576 A | 10/1997 | Henry |
| 5,695,480 A | 12/1997 | Evans et al. |
| 5,695,740 A | 12/1997 | Porter |
| 5,698,271 A | 12/1997 | Liberti et al. |
| 5,701,899 A | 12/1997 | Porter |
| 5,715,824 A | 2/1998 | Unger et al. |
| 5,716,981 A | 2/1998 | Hunter et al. |
| 5,718,884 A | 2/1998 | Klaveness et al. |
| 5,723,269 A | 3/1998 | Akagi et al. |
| 5,725,534 A | 3/1998 | Rasmussen |
| 5,733,925 A | 3/1998 | Kunz et al. |
| 5,741,331 A | 4/1998 | Pinchuk |
| 5,746,734 A | 5/1998 | Dormandy, Jr. et al. |
| 5,752,974 A | 5/1998 | Rhee et al. |
| 5,756,127 A | 5/1998 | Grisoni et al. |
| 5,760,097 A | 6/1998 | Li et al. |
| 5,766,147 A | 6/1998 | Sancoff et al. |
| 5,770,222 A | 6/1998 | Unger et al. |
| 5,779,668 A | 7/1998 | Grabenkort |
| 5,785,642 A | 7/1998 | Wallace et al. |
| 5,785,682 A | 7/1998 | Grabenkort |
| 5,792,478 A | 8/1998 | Lawin et al. |
| 5,795,562 A | 8/1998 | Klaveness et al. |
| 5,797,953 A | 8/1998 | Tekulve |
| 5,807,323 A | 9/1998 | Kriesel et al. |
| 5,813,411 A | 9/1998 | Van Bladel et al. |
| 5,823,198 A | 10/1998 | Jones et al. |
| 5,827,502 A | 10/1998 | Klaveness et al. |
| 5,827,531 A | 10/1998 | Morrison et al. |
| 5,830,178 A | 11/1998 | Jones et al. |
| 5,833,361 A | 11/1998 | Funk |
| 5,840,387 A | 11/1998 | Berlowitz-Tarrant et al. |
| 5,846,518 A | 12/1998 | Yan et al. |
| 5,853,752 A | 12/1998 | Unger et al. |
| 5,855,615 A | 1/1999 | Bley et al. |
| 5,863,957 A | 1/1999 | Li et al. |
| 5,876,372 A | 3/1999 | Grabenkort et al. |
| 5,877,224 A | 3/1999 | Brocchini et al. |
| 5,885,216 A | 3/1999 | Evans, III et al. |
| 5,885,547 A | 3/1999 | Gray |
| 5,888,546 A | 3/1999 | Ji et al. |
| 5,888,930 A | 3/1999 | Smith et al. |
| 5,891,155 A | 4/1999 | Irie |
| 5,894,022 A | 4/1999 | Ji et al. |
| 5,895,398 A | 4/1999 | Wensel et al. |

| | | | | | | |
|---|---|---|---|---|---|---|
| 5,895,411 | A | 4/1999 | Irie | 6,545,097 B2 | 4/2003 | Pinchuk et al. |
| 5,899,877 | A | 5/1999 | Leibitzki et al. | 6,575,896 B2 | 6/2003 | Silverman et al. |
| 5,902,832 | A | 5/1999 | Van Bladel et al. | 6,602,261 B2 | 8/2003 | Greene, Jr. et al. |
| 5,902,834 | A | 5/1999 | Porrvik | 6,602,524 B2 | 8/2003 | Batich et al. |
| 5,922,025 | A | 7/1999 | Hubbard | 6,605,111 B2 | 8/2003 | Bose et al. |
| 5,922,304 | A | 7/1999 | Unger | 6,629,947 B1 | 10/2003 | Sahatjian et al. |
| 5,928,626 | A | 7/1999 | Klaveness et al. | 6,632,531 B2 | 10/2003 | Blankenship |
| 5,935,553 | A | 8/1999 | Unger et al. | 6,652,883 B2 | 11/2003 | Goupil et al. |
| 5,951,160 | A | 9/1999 | Ronk | 6,680,046 B1 | 1/2004 | Boschetti |
| 5,957,848 | A | 9/1999 | Sutton et al. | 6,699,222 B1 | 3/2004 | Jones et al. |
| 5,959,073 | A | 9/1999 | Schlameus et al. | 7,591,993 B2 | 9/2009 | Boschetti |
| 6,003,566 | A | 12/1999 | Thibault et al. | 2001/0001835 A1 | 5/2001 | Greene, Jr. et al. |
| 6,015,546 | A | 1/2000 | Sutton et al. | 2001/0016210 A1 | 8/2001 | Mathiowitz et al. |
| 6,027,472 | A | 2/2000 | Kriesel et al. | 2001/0036451 A1 | 11/2001 | Goupil et al. |
| 6,028,066 | A | 2/2000 | Unger | 2001/0051670 A1 | 12/2001 | Goupil et al. |
| 6,047,861 | A | 4/2000 | Vidal et al. | 2002/0054912 A1 | 5/2002 | Kim et al. |
| 6,048,908 | A | 4/2000 | Kitagawa | 2002/0061954 A1 | 5/2002 | Davis et al. |
| 6,051,247 | A | 4/2000 | Hench et al. | 2002/0160109 A1 | 10/2002 | Yeo et al. |
| 6,056,721 | A | 5/2000 | Shulze | 2002/0182190 A1 | 12/2002 | Naimark et al. |
| 6,056,844 | A | 5/2000 | Guiles et al. | 2002/0197208 A1 | 12/2002 | Ruys et al. |
| 6,059,766 | A | 5/2000 | Greff | 2003/0007928 A1 | 1/2003 | Gray |
| 6,063,068 | A | 5/2000 | Fowles et al. | 2003/0032935 A1 | 2/2003 | Damiano et al. |
| 6,071,495 | A | 6/2000 | Unger et al. | 2003/0108614 A1 | 6/2003 | Volkonsky et al. |
| 6,071,497 | A | 6/2000 | Steiner et al. | 2003/0185895 A1 | 10/2003 | Lanphere et al. |
| 6,073,759 | A | 6/2000 | Lamborne et al. | 2003/0185896 A1 | 10/2003 | Buiser et al. |
| 6,090,925 | A | 7/2000 | Woiszwillo et al. | 2003/0187320 A1 | 10/2003 | Freyman |
| 6,096,344 | A | 8/2000 | Liu et al. | 2003/0194390 A1 | 10/2003 | Krall et al. |
| 6,099,864 | A | 8/2000 | Morrison et al. | 2003/0206864 A1 | 11/2003 | Mangin |
| 6,100,306 | A | 8/2000 | Li et al. | 2003/0215519 A1 | 11/2003 | Schwarz et al. |
| 6,139,963 | A | 10/2000 | Fujii et al. | 2004/0076582 A1 | 4/2004 | DiMatteo et al. |
| 6,149,623 | A | 11/2000 | Reynolds | 2004/0091543 A1 | 5/2004 | Bell et al. |
| 6,160,084 | A | 12/2000 | Langer et al. | 2004/0092883 A1 | 5/2004 | Casey, III et al. |
| 6,162,377 | A | 12/2000 | Ghosh et al. | 2004/0096662 A1 | 5/2004 | Lanphere et al. |
| 6,165,193 | A | 12/2000 | Greene, Jr. et al. | 2004/0101564 A1 | 5/2004 | Rioux et al. |
| 6,179,817 | B1 | 1/2001 | Zhong | 2004/0186377 A1 | 9/2004 | Zhong et al. |
| 6,191,193 | B1 | 2/2001 | Lee et al. | 2005/0025800 A1 | 2/2005 | Tan |
| 6,214,331 | B1 | 4/2001 | Vanderhoff et al. | 2005/0037047 A1 | 2/2005 | Song |
| 6,214,384 | B1 | 4/2001 | Pallado et al. | | | |
| 6,224,630 | B1 | 5/2001 | Bao et al. | | | |
| 6,224,794 | B1 | 5/2001 | Amsden et al. | | | |

FOREIGN PATENT DOCUMENTS

| | | |
|---|---|---|
| CA | 2326977 | 10/1999 |
| DE | 3834705 | 4/1990 |
| DE | 94 14 868.6 | 12/1994 |
| DE | 297 24 255 U1 | 10/2000 |
| DE | 100 26 620 | 3/2002 |
| EP | 0 067 459 | 12/1982 |
| EP | 0 122 624 | 10/1984 |
| EP | 0 123 235 | 10/1984 |
| EP | 0 243 165 | 10/1987 |
| EP | 0 294 206 | 12/1988 |
| EP | 0 402 031 | 12/1990 |
| EP | 0 422 258 | 4/1991 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 6/1994 |
| EP | 0 623 012 | 11/1994 |
| EP | 0 706 376 | 4/1996 |
| EP | 0 730 847 | 9/1996 |
| EP | 0 744 940 | 12/1996 |
| EP | 0 764 047 | 3/1997 |
| EP | 0 797 988 | 10/1997 |
| EP | 0 993 337 | 4/2000 |
| ES | 2 096 521 | 3/1997 |
| JP | 59-196738 | 11/1984 |
| JP | 62-45637 | 2/1987 |
| JP | 4-74117 | 3/1992 |
| JP | 6-57012 | 3/1994 |
| JP | 7-508048 | 9/1995 |
| JP | 9-110678 | 4/1997 |
| JP | 9-165328 | 6/1997 |
| JP | 9-316271 | 12/1997 |
| JP | 10-130329 | 5/1998 |
| JP | 2000189511 | 7/2000 |
| JP | 2001079011 | 3/2001 |
| JP | 2002-017848 | 1/2002 |
| JP | 2002-538194 | 11/2002 |
| NZ | 255409 | 2/1997 |
| NZ | 517377 | 8/2003 |

| | | | |
|---|---|---|---|
| 6,235,224 | B1 | 5/2001 | Mathiowitz et al. |
| 6,238,403 | B1 | 5/2001 | Greene, Jr. et al. |
| 6,245,090 | B1 | 6/2001 | Gilson et al. |
| 6,251,661 | B1 | 6/2001 | Urabe et al. |
| 6,258,338 | B1 | 7/2001 | Gray |
| 6,261,585 | B1 | 7/2001 | Sefton et al. |
| 6,264,861 | B1 | 7/2001 | Tavernier et al. |
| 6,267,154 | B1 | 7/2001 | Felicelli et al. |
| 6,268,053 | B1 | 7/2001 | Woiszwillo et al. |
| 6,277,392 | B1 | 8/2001 | Klein |
| 6,280,457 | B1 | 8/2001 | Wallace et al. |
| 6,291,605 | B1 | 9/2001 | Freeman et al. |
| 6,296,604 | B1 | 10/2001 | Garibaldi et al. |
| 6,296,622 | B1 | 10/2001 | Kurz et al. |
| 6,296,632 | B1 | 10/2001 | Luscher et al. |
| 6,306,418 | B1 | 10/2001 | Bley |
| 6,306,419 | B1 | 10/2001 | Vachon et al. |
| 6,306,425 | B1 | 10/2001 | Tice et al. |
| 6,306,427 | B1 | 10/2001 | Annonier et al. |
| 6,312,407 | B1 | 11/2001 | Zadno-Azizi et al. |
| 6,312,942 | B1 | 11/2001 | Plüss-Wenzinger et al. |
| 6,315,709 | B1 | 11/2001 | Garibaldi et al. |
| 6,335,384 | B1 | 1/2002 | Evans et al. |
| 6,344,182 | B1 | 2/2002 | Sutton et al. |
| 6,355,275 | B1 | 3/2002 | Klein |
| 6,364,823 | B1 | 4/2002 | Garibaldi et al. |
| 6,368,658 | B1 | 4/2002 | Schwarz et al. |
| 6,379,373 | B1 | 4/2002 | Sawhney et al. |
| 6,388,043 | B1 | 5/2002 | Langer et al. |
| 6,394,965 | B1 | 5/2002 | Klein |
| 6,423,332 | B1 | 7/2002 | Huxel et al. |
| 6,432,437 | B1 | 8/2002 | Hubbard |
| 6,436,112 | B2 | 8/2002 | Wensel et al. |
| 6,443,941 | B1 | 9/2002 | Slepian et al. |
| 6,458,296 | B1 | 10/2002 | Heinzen et al. |
| 6,476,069 | B2 | 11/2002 | Krall et al. |
| 6,495,155 | B1 | 12/2002 | Tice et al. |
| 6,544,503 | B1 | 4/2003 | Vanderhoff et al. |
| 6,544,544 | B2 | 4/2003 | Hunter et al. |

| | | |
|---|---|---|
| TW | 421658 | 2/2001 |
| WO | WO 91/12823 | 5/1991 |
| WO | WO 92/21327 | 12/1992 |
| WO | WO 93/00063 | 1/1993 |
| WO | WO 93/19702 | 10/1993 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/37165 | 11/1996 |
| WO | WO 96/39464 | 12/1996 |
| WO | WO 98/04616 | 2/1998 |
| WO | WO 98/10798 | 3/1998 |
| WO | WO 98/26737 | 6/1998 |
| WO | WO 98/47532 | 10/1998 |
| WO | WO 99/00187 | 1/1999 |
| WO | WO 99/12577 | 3/1999 |
| WO | WO 99/43380 | 9/1999 |
| WO | WO 99/51278 | 10/1999 |
| WO | WO 99/57176 | 11/1999 |
| WO | WO 00/23054 | 4/2000 |
| WO | WO 00/32112 | 6/2000 |
| WO | WO 00/40259 | 7/2000 |
| WO | 00/53159 | 9/2000 |
| WO | 00/66183 | 11/2000 |
| WO | WO 00/71196 | 11/2000 |
| WO | WO 00/74633 | 12/2000 |
| WO | WO 01/12359 | 2/2001 |
| WO | WO 01/66016 | 9/2001 |
| WO | WO 01/70291 | 9/2001 |
| WO | WO 01/72281 | 10/2001 |
| WO | WO 01/76845 | 10/2001 |
| WO | WO 01/93920 | 12/2001 |
| WO | WO 02/11696 | 2/2002 |
| WO | WO 02/34298 | 5/2002 |
| WO | WO 02/34299 | 5/2002 |
| WO | WO 02/34300 | 5/2002 |
| WO | WO 02/43580 | 6/2002 |
| WO | WO 03/016364 | 2/2003 |
| WO | WO 03/051451 | 6/2003 |
| WO | WO 03/082359 | 10/2003 |
| WO | WO 2004/019999 | 3/2004 |
| WO | WO 2004/073688 | 9/2004 |
| WO | WO 2004/075989 | 9/2004 |

OTHER PUBLICATIONS

Barr, J.D., et al., "Polyvinyl Alcohol Foam Particles Sizes and Concentrations Injectable through Microcatheters", *JVIR*, vol. 9, No. 1, pp. 113-118; 1998.

Barton, P. et al., "Embolization of Bone Metastases," *Journal of Vascular and Interventional Radiology*, 7(1):81-88 (Jan.-Feb. 1996).

Battinelli, L. et al., "New Class of Poly(vinyl alcohol) Polymrs as Column-Chromatography Stationary Phases for Candida Rugosa Lipase Isoforms Separation", *J. Chromatogr A*, vol. 753, No. 1, pp. 47-55; 1996.

Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.*, 17:541-548, Mar. 1996.

Berenstein, A. et al., "Catheter and Material Selection for Transarterial Embolization: Technical Considerations. II. Materials.", *Radiology*, vol. 132, No. 3, pp. 631-639; 1979.

Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981.

Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.

Bourke et al., "Protein Drug Release from Photocrosslinked Poly(vinyl alcohol) Hydrogels," *Society for Biomaterials 28th Annual Meeting Transactions*, p. 144 (2002).

Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.

Brockmann, J. et al., "Radiolabeling of p-Bz-DOTA-CD-11c antibody with $^{88}$Y: Conjugation, Labeling, Biodistribution studies", 2 pages, 2000 http://www.kernchemie.uni-mainz.de/downloads/jb2000/b14_brockmann.pdf.

Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583, http://www.hepatitis-central.com/hcv/hcc/embolization/references.html.

Buhle, Jr. EL, "Re: Re: Hepatic Arterial Embolization", *UCLA Medicine Online*, Mar. 10, 1996, http://www.meds.com/archive/mol-cancer/1996/msg00128.html, 2 pages.

Burczak, et al., "Long-term in vivo performance and biocompatibility of poly (vinyl alcohol) hydrogel macrocapsules for hybrid-type artificial pancreas", *Biomaterials*, vol. 17, No. 24, pp. 2351-2356, 1996.

Burczak, et al., "Polymeric materials for biomedical purposes obtained by radiation methods. V. hybrid artificial pancreas", *Polim Med*, vol. 24, No. 1-2, pp. 45-55, 1994 (English Summary included).

Capozza et al., "Endoscopic treatment of vesico-ureteric reflux and urinary incontinence: technical problems in the paediatric patient," *British Journal of Urology*, 75(4):538-542 (Apr. 1995).

Carroll, B.A. et al., "Microbubbles as Ultrasonic Contrast Agents", *Investigative Radiology*, vol. 14, No. 3, p. 374, Supplement to May-Jun. 1979.

Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.

Carstensen, E.L. et al., "Determination of the Acoustic Properties of Blood and its Components", *Journal of Acoustical Society of America*, vol. 25, No. 2, pp. 286-289, Mar. 1953.

Choe, et al., "An experimental study of embolic effect according to infusion rate and concentration of suspension in transarterial particulate embolization", *Invest Radiol*, vol. 32, No. 5, pp. 260-270, 1997.

Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25, Oct. 1982.

Cirkel, U. et al., "Experience with Leuprorelin Acetate Depot in the Treatment of Fibroids: A German Multicentre Study", *Clinical Therapeutics*, vol. 14, Suppl. A, 1992.

Clarian Health Methodist—Indiana Lions Gamma Knife Center, "Arteriovenous Malformation," http://www.clarian.com/tyhealth/gammaknife/cond_arter.asp, 4 pages, Last Updated on Mar. 20, 2000.

Colombo M, "Treatment of Hepatocellular Carcinoma", *Journal of Viral Hepatitis*, 4(Suppl. 1):125-130 (1997), http://home.texoma.net/~ moreland/stats/hcc-9.html.

Concentric Medical, Inc.—Product Information (3 pages), 2002.

Cruise et al., "In Vitro and In Vivo Characterization of a Hydrogel-Based Aneurysm Embolization System," *Society for Biomaterials 28th Annual Meeting Transactions*, p. 203 (2002).

Deasy, P. B., "*Microencapsulation and Related Drug Processes*", New York, NY, Marcel Dekker, Inc., 345 pages, 1984 (Table of Contents only).

de Gast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.

Derdeyn, et al., "Collagen-coated acrylic microspheres for embolotherapy: in vivo and in vitro characteristics", *American Journal of Neuroradiology*, vol. 18, No. 4, pp. 647-653, 1997.

Derdeyn, et al., "Polyvinyl alcohol particle size and suspension characteristics", *American Journal of Neuroradiology*, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", *Journal of Pharmaceutical Sciences*, vol. 83, No. 1, pp. 104-106, Jan. 1994.

Duckwiler et al., "Catheters, embolic agents spark neurointervention," *Diagnostic Imaging*, 16(5):66-72 (May 1994).

Ersek et al., "Bioplastique: A New Textured Copolymer Microparticle Promises Permanence in Soft-Tissue Augmentation," *Plastic and Reconstructive Surgery*, 87(4):693-702 (Apr. 1991).

Eskridge, "Interventional Neuroradiology," *Radiology*, 172:991-1006 (Nov. 1989).
Feldman, L. et al., "Transcatheter Vessel Occlusion: Angiographic Results Versus Clinical Success", *Radiology*, vol. 147, pp. 1-5, Apr. 1983.
Ferrofluids, Physical Properties and Applications Ferrofluidics Corp., Nashua, NH, 5 pages, 1986.
FeRx Incorporated, FeRx Profile http://www.biotechshares.com/FERX.htm, 4 pages (Retrieved from the internet on Jun. 26, 2003).
Fritzsch, T. et al., "SH U 508, A Transpulmonary Echocontrast Agent", *Investigative Radiology*, vol. 25, Supplement 1, pp. S160-S161, Sep. 1990.
Fujimoto, S. et al., "Biodegradable Mitomycin C Microspheres Given Intra-Arterially for Inoperable Hepatic Cancer", *Cancer*, vol. 56, pp. 2404-2410, 1985.
Gander, et al., "Effect of polymeric network structure on drug release from cross-linked poly(vinyl alcohol) micromatrices", *Pharm Res*, vol. 6, No. 7, pp. 578-584, 1989.
Germano, et al., "Histopathological follow-up study of 66 cerebral arteriovenous malformations after therapeutic embolization with polyvinyl alcohol", *J Neurosurg*, vol. 76, No. 4, pp. 607-614, 1992.
Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, vol. 11, No. 10, pp. 1244-1255, Dec. 2000.
Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.
Gohel, et al., "Formulation design and optimization of modified-release microspheres of diclofenac sodium", *Drug Dev Ind Pharm*, vol. 25, No. 2, pp. 247-251, 1999.
Goldberg, B.B., "Ultrasonic Cholangiography", *Radiology*, vol. 118, pp. 401-404, Feb. 1976.
Goodwin, et al., "Overview of embolic agents and their indications", *Eleventh Annual International Symposium on Endovascular Therapy*, pp. 303-306, 1999.
Goodwin, et al., "Preliminary experience with uterine artery embolization for uterine fibroids", *Journal of Vascular and Interventional Radiology*, vol. 8, No. 4, pp. 517-526, 1997.
Gramiak et al., "Echocardiography of the Aortic Root," *Investigative Radiology*, 3(5):356-366 (Sep.-Oct. 1968).
Gramiak, R. et al., "Ultrasound Cardiography: Contrast Studies in Anatomy and Function", *Radiology*, vol. 92, No. 5, pp. 939-948, Apr. 1969.
Grandfils, et al., "Preparation of poly (D,L) lactide microspheres by emulsion solvent evaporation, and their clinical implications as a convenient embolic material", *J Biomed Mater Res*, vol. 26, No. 4, pp. 467-479, 1992.
Greenwood, L.H. et al., "Obstetric and Nonmalignant Gynecologic Bleeding: Treatment with Angiographic Embolization", *Radiology*, vol. 164, No. 1, pp. 155-159, Jul. 1987.
Gupta et al., "Plasma-induced graft polymerization of acrylic acid onto poly(ethylene terephthalate) films: characterization and human smooth muscle cell growth on grafted films," *Biomaterials*, 23:863-871 (2002).
Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3(4):710-723 (2002).
Hamada et al., "Embolization with Cellulose Porous Beads, II: Clinical Trial," *AJNR Am. J. Neuroradiol.*, 17:1901-1906 (Nov. 1996).
Hirano et al., "Transcutaneous Intrafold Injection For Unilateral Vocal Fold Paralysis: Functional Results," *Ann. Otol. Rhinol Laryngol.*, 99(8):598-604 (Aug. 1990).
Horak et al., "Hydrogels in endovascular embolization. I. Spherical particles of poly (2-hydroxyethyl methacrylate) and their medico-biological properties", *Biomaterials*, 7(3):188-192 (May 1986).
Horak et al., "Hydrogels in endovascular embolization. II. Clinical use of spherical particles", *Biomaterials*, 7(6):467-470 (Nov. 1986).
Huang et al., "Percutaneous endovascular embolization of intracerebral arteriovenous malformations. Experience in 72 cases", *Chin Med J*, vol. 108, No. 6, pp. 413-419, 1995.

"Injectable Tissue Implant Could Repair Ravages of Surgery", Clemson University, Biotech Week, Oct. 22, 2003, p. 117.
Jack, et al., "Radiolabeled polyvinyl alcohol particles: a potential agent to monitor embolization procedures", *Int J Rad Appl Instrum B*, vol. 13, No. 3, pp. 235-243, 1986.
Jiaqi, Y. et al., "A New Embolic Material: Super Absorbent Polymer (SAP) Microsphere and Its Embolic Effects," *Nippon Acta Radiologica*, 56:19-24 (1996) (English Abstract included).
Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.iop.org/Journals/pb.
Joy C, et al., "Use of Preoperative Embolization in the Treatment of Vascular Metastatic Lesions of the Spine," http://www.aaos.org/wordhtml/anmeet91/scipro/ppr472.htm, Mar. 12, 1991.
Jung et al., "Sulfobutylated poly(vinyl alcohol)-graft-poly(lactide-co-glycolide)s facilitate the preparation of small negatively charged biodegradable nanospheres," *Journal of Controlled Release*, 67:157-169 (2000).
Kai, et al., "The utility of the microcrystalline cellulose sphere as a particulate embolic agent: an experimental study", *American Journal of Radiology*, vol. 21, No. 6, pp. 1160-1163, 2000.
Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.
Kan, et al., "In vivo microscopy of the liver after injection of lipiodol into the hepatic artery and portal vein in the rat", *Acta Radiologica*, vol. 30, pp. 419-425, 1989.
Kerber, C., "Balloon Catheter with a Calibrated Leak", *Radiology*, vol. 120, pp. 547-550, Sep. 1976.
Kerber et al., "Polyvinyl Alcohol Foam: Prepackaged Emboli for Therapeutic Embolization", *American Journal Roentgenol*, vol. 130, pp. 1193-1194, Jun. 1978.
Kerber, "Flow-Controlled Therapeutic Embolization: A Physiologic and Safe Technique", *AJR*, vol. 134, pp. 557-561, Mar. 1980.
Khankan et al., "Embolic Effects of Superabsorbent Polymer Microspheres in Rabbit Renal Model: Comparison with Tris-acryl Gelatin Microspheres and Polyvinyl Alcohol," *Radiation Medicine*, 22(6):384-390 (2004).
Kim, et al., "Composite poly(vinyl alcohol) beads for controlled drug delivery", *Pharm Res*, vol. 9. No. 1, pp. 10-16, 1992.
Kim et al., "Hollow Silica Spheres of Controlled Size and Porosity by Sol-Gel Processing," *J. Am. Ceram. Soc.*, 74(8):1987-1992 (Aug. 1991).
Kim et al., "Poly(vinyl alcohol) beads with core-shell structure for drug delivery," *Cosmetic and Pharmaceutical Applications of Polymers*, Plenum Press, New York, pp. 209-214 (1991).
Kim et al., "Suspension polymerized poly(vinyl alcohol) beads for drug delivery," *Polymeric Materials: Science and Engineering, Proceedings of the ACS Division of Polymeric Materials: Science and Engineering*, 63:64-67 (1990).
Krinick et al., "A polymeric drug delivery system for the simultaneous delivery of drugs activatable by enzymes and/or light," *J. Biomater. Sci. Polymer Edn*, 5(4):303-324 (1994).
Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.
Kurata, et al., "Preoperative embolization for meningiomas using PVA particles", *No Shinkei Geka*, vol. 20, No. 4, pp. 367-373, 1992 (English Abstract included).
Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp (English Abstract included).
Kurosaki et al., "Evaluation of PVA-Gel Spheres as GI-Transit Time Controlling Oral Drug Delivery System", *Proceedings of the 19th International Symposium on Controlled Release of Bioactive Materials*, Orlando, Florida, pp. 273-274, Jul. 26-31, 1992.
Kusano, et al., "Low-dose particulate polyvinylalcohol embolization in massive small artery intenstinal hemorrahage. Experimental and clinical results", *Invest Radiol*, vol. 22, No. 5, pp. 388-392, 1987.

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", *Rontgenblatter*, vol. 36, No. 1, pp. 10-14, 1983 (English Abstract included).

Latchaw et al., "Polyvinyl Foam Embolization of Vascular and Neoplastic Lesions of the Head, Neck, and Spine", *Radiology*, vol. 131, pp. 669-679, Jun. 1979.

Laurent, "Materials and biomaterials for interventional radiology," *Biomed. & Pharmacother.*, 52:76-88 (1998).

Lemperle et al., "PMMA Microspheres for Intradermal Implantation: Part I. Animal Research," *Annals of Plastic Surgery*, 26(1):56-63 (Jan. 1991).

Lendlein, A. et al., "Biodegradable, Elastic Shape-Memory Polymers for Potential Biomedical Applications", *Science*, vol. 296, pp. 1673-1676, May 31, 2002.

Leung et al., "Determinants of Postembolization Syndrome after Hepatic Chemoembolization", *Journal of Vascular and Interventional Radiology*, vol. 12, No. 3, pp. 320-326, Mar. 2001.

Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.

Levy et al., "Transcatheter Uterine Artery Embolization for the Treatment of Symptomatic Uterine Fibroid Tumors," *Journal of Women's Imaging*, 2(4):168-175 (2000).

Lipman, "Uterine artery embolization for the treatment of symptomatic uterine fibroids: A review," *Applied Radiology*, 29(7):15-20 (Jul. 2000).

Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.

Markoff, et al., "Uterine arteriovenous malformation successfully embolized with a liquid polymer, isobutyl 2-cyanoacrylate", *Am. J. Obstet. Gynecol.*, 155:659-660 (Sep. 1986).

Markus et al., "Experimental Aspects of High-Intensity Transient Signals in the Detection of Emboli," *J. Clin. Ultrasound.*, 23(2):81-87 (Feb. 1995).

Maruhashi, "Modified Polyvinyl Alcohols I and II," *Polyvinyl Alcohol—Developments*, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.

Matsumaru, et al., "Embolic materials for endovascular treatment of cerebral lesions", *J Biomater Sci Polym Ed*, vol. 8, No. 7, pp. 555-569, 1997.

Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", *Neurosurgery*, vol. 53, No. 2, pp. 402-408, Aug. 2003.

Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

Mavligit, G. et al., "Gastrointestinal Leiomyosarcoma Metastatic to the Liver," *Cancer*, 75(8):2083-2088 (Apr. 15, 1995).

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

Mid-America Interventional Radiological Society, "New Treatment for Uterine Fibroids Avoids Surgery," http://www.mirs.org/fibroids.htm, 6 pages, Submitted in Oct. 1999.

Moroz, P. et al., "Arterial Embolization Hyperthermia in Porcine Renal Tissue", *Journal of Surgical Research*, vol. 105, No. 2, pp. 209-214, Jun. 15, 2002.

Moroz, P. et al., "Hepatic Clearance of Arterially Infused Ferromagnetic Particles", *Int. J. Hyperthermia*, vol. 19, No. 1, pp. 23-24, Feb. 2003, http://www.tandf.co.uk/journals.

Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997.

Nakstad, et al., "Embolization of intracranial arteriovenous malformations and fistulas with polyvinyl alcohol particles and platinum fibre coils", *Neuroradiology*, vol. 34, No. 4, pp. 348-351, 1992.

Namiki, "Application of Teflon Paste for Urinary Incontinence—Report of 2 Cases," *Uro. Int.*, 39:280-282 (1984).

Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997.

Nikishin LF et al., "Interventional radiology in diffuse toxic goiter", *European Congress of Radiology*, Abstract 9041, 1999, http://www.ecr.org/conferences/ecr1999/sciprg/abs/p090041.htm, 7 pages.

Ophir, et al., "Ultrasonic backscatter from contrast producing collagen microspheres", *Ultrasonic Imaging*, vol. 2, pp. 67-77, 1980.

Orienti et al., "Crosslinked Polyvinylalcohol Hydrogels as Vehicles for Hydrophilic Drugs," *Arch. Pharm. Pharm. Med. Chem.*, 333:421-424 (2000).

Orsini, L. F. et al., "Pelvic Organs in Premenarcheal Girls: Real-Time Ultrasonography", *Radiology*, vol. 153, No. 1, pp. 113-116, Oct. 1984.

Parker, et al., "A particulate contrast agent with potential for ultrasound imaging of liver", *Ultrasound in Medicine and Biology*, vol. 13, No. 9, pp. 555-566, 1987.

Pedley et al., "Hydrogels in Biomedical Applications," *British Polymer Journal*, 12:99-110 (Sep. 1980).

Pesant A.C. et al., "Dural fistulas involving the cavernous sinus: Treatment by embolization—7 cases", *European Congress of Radiology*, Abstract 3-088, 1997, http://www.ecr.org/conferences/ecr1997/sciprg/abs/9703088p.htm, 1 page.

Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.

Pistel et al., "Brush-like branched biodegradable polyesters, part III Protein release from microspheres of poly(vinyl alcohol)-graft-poly(D,L-lactic-co-glycolic acid)," *Journal of Controlled Release*, 73:7-20 (2001).

Politano et al., "Periurethral Teflon Injection for Urinary Incontinence," *The Journal of Urology*, 111:180-183 (1974).

Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.

Pritchard, et al., "Poly(Vinyl Alcohol): Basic Properties and Uses", London, England: Gordon and Breach Science Publishers, pp. 95-97, 1970.

Progelhof et al., "Table 4.21. Properties of electrical insulating films (101)," *Polymer Engineering Principles: Properties, Processes, and Tests for Design*, Hanser Publishers, Munich, p. 383 (1993).

Purdy, et al., "Arteriovenous malformations of the brain: choosing embolic materials to enhance safety and ease of excision", *J Neurosurg*, vol. 77, No. 2, pp. 217-222, 1992.

PVA Plus, AngioDynamics® Inc., "Reliable PVA Foam Formulated for Consistency and Controlled Delivery—Embolization Particles Ordering Information," www.angiodynamics.com, 2 pages (Aug. 2002).

Quisling, et al., "Histopathology analysis of intraarterial polyvinyl alcohol microemboli in rat cerebral cortex", *American Journal of Neuroradiology*, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, vol. 12, No. 2, pp. 187-193, Feb. 2001.

Ramos, et al., "Tumor vascular signals in renal masses: detection with Doppler US", *Radiology*, vol. 168, No. 3, pp. 633-637, 1988.

Ravina, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (English Abstract included).

Ravina, J.H. et al., "Arterial Embolisation to Treat Uterine Myomata", *Lancet*, vol. 346, pp. 671-674, Sep. 9, 1995.

Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (English Summary included).

Repa, I. et al., "Mortalities Associated with Use of a Commercial Suspension of Polyvinyl Alcohol," *Radiology*, 170(2):395-399 (Feb. 1989).

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Rump, A. et al., "Pharmacokinetics of Intraarterial Mitomycin C in the Chemoembolisation Treatment of Liver Metastases," *Gen. Pharmac.*, 27(4):669-671 (1996).

Schetky, "Shape-Memory Alloys," *Encyclopedia of Chemical Technology*, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.

Schwarz et al., "The acoustic filter: An ultrasonic blood filter for the heart-lung machine," *J. Thorac. Cardiovasc. Surg.*, 104(6):1647-1653 (Dec. 1992).

Shafik, "Intraesophageal Polytef injection for the treatment of reflux esophagitis," *Surg. Endosc.*, 10:329-331 (1996).

Shape Shifters, http://www.sciam.com/tehbiz/0501scicit6.html, 3 pages, 2001.

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," *J. Vasc. Interv. Radiol.*, 14:89-98 (2003).

Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.

"Smart Sutures Tie Themselves", Apr. 26, 2002, http://www.sciam.com/article.cfm?articleID=0047706-121F-1CD0-B4A8809EC588, 2 pages.

Smith et al., "Evaluation of Polydimethylsiloxane as an alternative in the Endoscopic Treatment of Vesicoureteral Reflux," *The Journal of Urology*, 152:1221-1224 (Oct. 1994).

Smith et al., "Left Heart Opacification with Peripheral Venous Injection of a New Saccharide Echo Contrast Agent in Dogs", *JACC*, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," *J. Biomater. Sci. Polymer Edn*, 11(1):27-43 (2000).

Spickler, et al., "The MR appearance of endovascular embolic agents in vitro with clinical correlation", *Comput Med Imaging Graph*, vol. 14, No. 6, pp. 415-423, 1990.

Spies JB, "Georgetown University Medical Center. Uterine Fibroid Embolization (UFE). An alternative to surgery for patients with uterine fibroids. Literature Review," http://www.fibroidoptions.com/pr-lit.htm, 6 pages, Sep. 1, 2001.

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Stridbeck, H. et al, "Collateral Circulation Following Repeated Distal Embolization of the Hepatic Artery in Pigs," *Invest. Radiol.*, 19(3):179-183 (1984).

Strunk, et al., "Treatment of congenital coronary arteriovenous malformations with microparticle embolization", *Cathet Cardiovasc Diagn*, vol. 22, No. 2, pp. 133-136, 1991.

Swanson DA et al., "The role of embolization and nephrectomy in the treatment of metastatic renal carcinoma", *Urologic Clinics of North America*, 7(3):719-730, 1980. University of Pennsylvania Cancer Center—Oncolink, http://www.oncolink.upenn.edu/pdg_html/cites/00/00585.html.

Tabata et al., "Tumor accumulation of poly(vinyl alcohol) of different sizes after intravenous injection", *Journal of Controlled Release*, vol. 50, pp. 123-133, Jan. 2, 1998.

Tadavarthy et al., "Polyvinyl Alcohol (Ivalon)—A New Embolic Material", *The American Journal of Roentgenology Radium Therapy and Nuclear Medicine*, vol. 125, No. 3, pp. 609-616, Nov. 1975.

Tadavarthy et al., "Polyvinyl Alcohol (Ivalon) as an Embolizing Agent", *Seminars in Interventional Radiology*, vol. 1, No. 2, pp. 101-109, Jun. 1984.

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Tao, et al., "Study of microspheres for embolization of hepatic artery", *Acta Pharmaceutica Sinica*, vol. 23, No. 1, pp. 55-60, 1988.

Tao, et al., "Study of microspheres for embolization of hepatic artery", (Translation) *Acta Pharmaceutica Sinica*, vol. 23, No. 1, pp. 55-60, 1988.

Terada, et al., "Preoperative embolization of meningiomas fed by ophthalmic branch arteries", *Surg Neurol*, vol. 45, No. 2, pp. 161-166, 1996.

Thanoo, et al., "Controlled release of oral drugs from cross-linked polyvinyl alcohol microspheres", *J Pharm Pharmacol*, vol. 45, No. 1, pp. 16-20, 1993.

Thanoo, B. C. et al., "Preparation and Properties of Barium Sulphate and Methyl Iothalamate Loaded Poly(vinyl Alcohol) Microspheres as Radiopaque Particulate Emboli," *Journal of Applied Biomaterials*, 2:67-72 (1991).

Thanoo, et al., "Tantalum loaded silicone micropsheres as particulate emboli", *J Microencapsul*, vol. 8, No. 1, pp. 95-101, 1991.

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976 (English Abstract included).

The Vanderbilt-Ingram Cancer Center, "Kidney Cancer," http://www.mc.Vanderbilt.Edu/cancer/cancerinfo/kidney.html, 1 page, 2001.

Tian et al., "Design and synthesis of amphiphilic poly (ethylene glycol) derivatives as micellar drug delivery systems," *Polymer Preprints*, 43(2):719-720 (Fall 2002).

Tikkakoski, et al., "Preoperative embolization in the management of neck paragangliomas", *Laryngoscope*, vol. 107, pp. 821-826, 1997.

Toon, "Improving a Key Weapon Against Cancer," *Research Horizons*, pp. 11-12, Spring/Summer 2001.

Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148-156, 1994.

University Medical Center SUNY Stony Brook, Department of Urology, "Variococele and its treatment," http://www.hsc.sunysb.edu/urology/male_inf...variocoele_and_its_treatment.html, 8 pages, Last Updated on Mar. 12, 2001.

Vivas S et al., "Arterioportal fistula and hemobilia in a patient with hepatic transplant", Gastroenterol Hepatol, 21(2):88-9, http://www.doyma.es/copiani/revistas/gastro/abstr/abs_p080.html, Feb. 1998 (English Abstract included).

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2 pages, 2002.

Walsh RM et al., "Role of Angiography and Embolization for Acute Massive Upper Gastronintestinal Hemorrhage," *J. Gastrointest. Surg.*, 3:61-66 (1999).

Waltman, A.C. et al., "Technique for Left Gastric Artery Catheterization", *Radiology*, vol. 109, No. 3, pp. 732-734, Dec. 1973.

White, Jr., "Embolotherapy in Vascular Disease," *American Journal of Roentgenology*, 142:27-30 (Jan. 1984).

Widder, K.J. et al., "Selective Targeting of Magnetic Microspheres Containing Adriamycin: Total Remission in Yoshida Sarcoma-Bearing Rats", *Proceedings of the 16th Annual Meeting of American Society of Clinical Oncology*, May 26-27, 1980, San Diego, CA, p. 261.

Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.

Wikholm G et al., "Embolization of Cerebral Arteriovenous Malformations: Part I—Technique, Morphology, and Complications", *Neurosurgery*, 39(3):448-459 (Sep. 1996).

Winters et al., "Periurethral injection of collagen in the treatment of intrinsic sphincteric deficiency in the female patient," *The Urologic Clinics of North America*, 22(3):673-678 (Aug. 1995).

Worthington-Kirsch RL, "Interventionalists offer management option for uterine fibroids," *Diagnostic Imaging*, 21(3):47-49, Mar. 1999, http://www.dimag.com/references/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Wright, K.C. et al., "Partial Splenic Embolization Using Polyvinyl Alcohol Foam, Dextran, Polystyrene, or Silicone," *Radiology*, 142:351-354, Feb. 1982.

Wu, A.M., "Engineered Antibodies for Breast Cancer Imaging and Therapy," http://www.cbcrp.org/research/PageGrant.asp?grant_id=111, 3 pages, 1996.

Yamada, T. et al., "Extended Intraarterial Cisplatin Infusion for Treatment of Gynecologic Cancer After Altercation of Intrapelvic Blood Flow and Implantation of a Vascular Access Device", *Cardiovasc. Intervent. Radiol.*, vol. 19, pp. 139-145, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Surface Immobilization of Galactose onto Aliphatic Biodegradable Polymers for Hepatocyte Culture," *Biotechnol. Bioeng.*, 78(1):1-10 (Apr. 5, 2002).

Yusi et al., "Submuscosal Injection of Polyvinyl Alcohol in Artificially Created Vesico-Ureteral Reflux: A Preliminary Report," *Asian J. Surg.*, 18(2):122-127 (Apr. 1995).

Zisch et al., "Covalently conjugated VEGF-fibrin matrices for endothelialization," *Journal of Controlled Release*, 72:101-113 (2001).

Ziskin, M.C. et al., "Contrast Agents for Diagnostic Ultrasound", *Investigative Radiology*, vol. 7, No. 6, pp. 500-505, Nov.-Dec. 1972.

Zou, Ying-hua, et al. "Experimental Canine Hapatic Artery Embolization with Polyvinyl Alcohol Microspheres," *Zhong Hua Fang-She Xue ZaZhi*, 23(6):330-332 (1989).

Zou, Ying-hua, et al. "Experimental Canine Hapatic Artery Embolization with Polyvinyl Alcohol Microspheres," Translation, *Zhong Hua Fang-She Xue ZaZhi*, 23(6):330-332 (1989).

ic agents can be delivered at desired dosages for an extended period of time.

DRUG DELIVERY PARTICLE

CROSS REFERENCE TO RELATED APPLICATION

The following is a continuation of U.S. Ser. No. 10/232,265, filed Aug. 30, 2002, now U.S. Pat. No. 7,462,366, the entire contents of which are hereby incorporated by reference. The entire contents of both of U.S. Pat. Nos. 7,094,369, and 7,588,780 are hereby incorporated by reference.

TECHNICAL FIELD

This invention relates to a drug delivery particle.

BACKGROUND

Therapeutic agents can be delivered systemically, for example, by injection through the vascular system or oral ingestion, or they can be applied directly to a site where treatment is desired. It is also often desirable that the therapeutic agent be delivered at desired dosages for an extended period of time.

SUMMARY

In a first aspect, the invention features a drug delivery device which includes a substantially spherical polymer particle having an internal reservoir region including relatively large pores containing therapeutic agent and a metering region substantially surrounding the reservoir region and having fewer relatively large pores.

In another aspect, the invention features a method of manufacturing a drug delivery particle by generating drops. For example, the method can include generating drops of a base polymer and a gelling compound, and combining the particles with a therapeutic agent.

In another aspect, the invention features a method of delivering a therapeutic agent to a patient. The method includes administering to a patient a substantially spherical polymer particle. The particle includes polyvinyl alcohol, and has an interior region having relatively large pores, a surface region having fewer relatively large pores, and a therapeutic agent carried by the particle.

Embodiments may include one or more of the following. The particle comprises PVA. The PVA is 1,3 diol acetalized. The polymer is modified by graft polymerization. The particle includes a polysaccharide. The polysaccharide is alginate. The particle has a coating of polymer. The coating is erodable. The coating covers a drug disposed on the surface of the particle. The therapeutic agent is effective for treatment of cancer. The particle has a sphericity of about 90% or more. The particle has a diameter of about 1 cm or less. The device is a collection of particles.

Embodiments may also include one or more of the following. The method includes reacting the base polymer and removing the gelling compound. The method includes drying the particle and exposing the dried particle to therapeutic agent. The method includes combining therapeutic agent prior to generating said drops. The gelling compound is a polysaccharide. The gelling compound is alginate. The method includes contacting the drops with a gelling agent. The method the gelling agent is a divalent agent. The base polymer is PVA. The method includes reacting the PVA by acetalization. The PVA has a molecular weight of about 75,000 g/mole or greater. The method includes modifying the viscosity of the base polymer and gelling compound prior to forming said drops. The method includes modifying the viscosity by heating. The method includes forming said drops by vibratory nebulization.

Embodiments may also include one or more of the following. The administration is by percutaneous injection. The administration is by a catheter. The therapeutic agent is effective treatment of uterine fibroids. Particles are delivered directly into a tissue mass. Particles are delivered through a body lumen, e.g., a vascular lumen. The particles can be used in embolic applications.

Embodiment may include one or more of the following advantages. A sustained, controlled-dosage release of therapeutic agents can be effected by a substantially spherical agent-containing particle that includes a reservoir region in its interior and a metering region surrounding the reservoir region which controls the release of the agent from the particle.

Other features, objects and advantages follow. For example, features of the particles, including sizes, pore profiles, compressibility, sphericity, and composition and the methods for making and administering, follow and can be found in U.S. Pat. No. 7,588,780.

DESCRIPTION OF DRAWINGS

FIG. 3A is a light micrograph of a collection of particles, while

FIG. 4A is a schematic of the manufacture of a particle while

DETAILED DESCRIPTION

Structure

Figure 1:
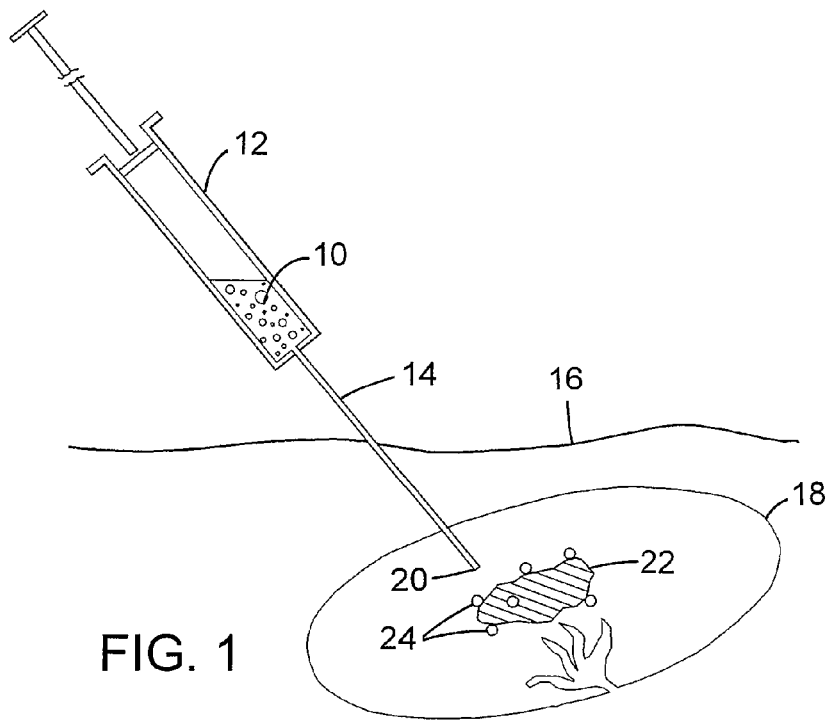
FIG. 1 is a schematic illustrating administration of drug delivery particles.

Referring to FIG. 1, a drug delivery composition 10 is injected using a syringe 12 with a needle 14 that is used to puncture the skin 16 and extend into the liver 18. The tip of the needle 20 is disposed within the tissue mass of the liver near and/or within a tumorous malignancy 22. The composition 10 includes a carrier fluid which carries drug delivery particles 24. The particles can be positioned about the lesion 22. In alternative embodiments, the particles can be delivered through the vasculature, e.g., by a catheter inserted into the hepatic artery. Another application includes treatment of uterine fibroids as described in U.S. Pat. No. 7,588,780, supra.

Figure 2:
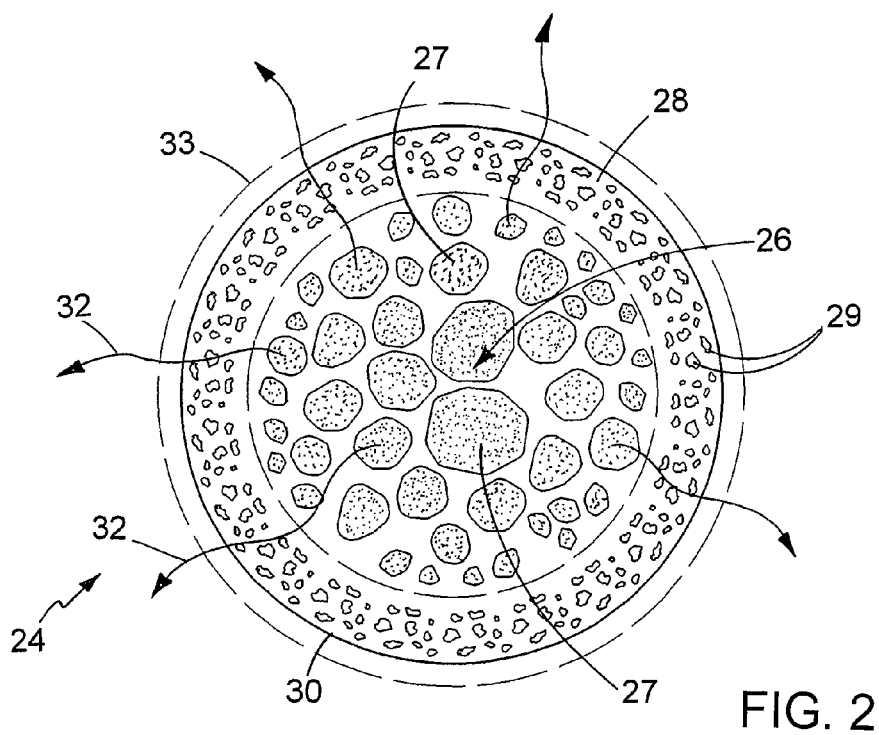
FIG. 2 is a cross-sectional schematic illustrating release of drug from a particle.

Referring particularly to FIG. 2, the particles are substantially spherical and include an interior reservoir region 26 which is characterized by relatively large pores 27 and a metering region 28 which is characterized by relatively small pores 29. The large pores 27 in the reservoir region hold a supply of a therapeutic agent, such as a tumor-toxic agent, which diffuses through interpore passageways into the metering region and is released from the surface 30 of the particle (arrows 32) to expose adjacent tissue. The porous structure of a particle is believed to create a therapeutic agent concentration gradient from relatively high therapeutic concentration in the reservoir region to lower concentrations in the metering region. The relative size of the pores in the regions and the relative thickness of the metering region control the rate of elution of therapeutic agent from the particle. The substantially spherical shape of the particle contributes to symmetric elution in all directions. In addition, the relatively uniform thickness of the metering region surrounding the reservoir region enhances uniformity of elution dosage.

The particles are substantially formed of a highly water-insoluble, high molecular weight polymer. As will be discussed further below, a preferred polymer is high molecular weight polyvinyl alcohol (PVA) that has been acetalized. Preferably, the embolic particles are substantially pure intra-chain 1,3 acetalized PVA and substantially free of animal derived residue such as collagen. In embodiments, the particles include a minor amount, e.g. less than about 0.2 weight %, of alginate or another polysaccharide or gelling material. The particle may also include an optional coating 33. The coating erodes in the body, e.g. on contact with body fluid, as will be discussed below.

Figure 3A:
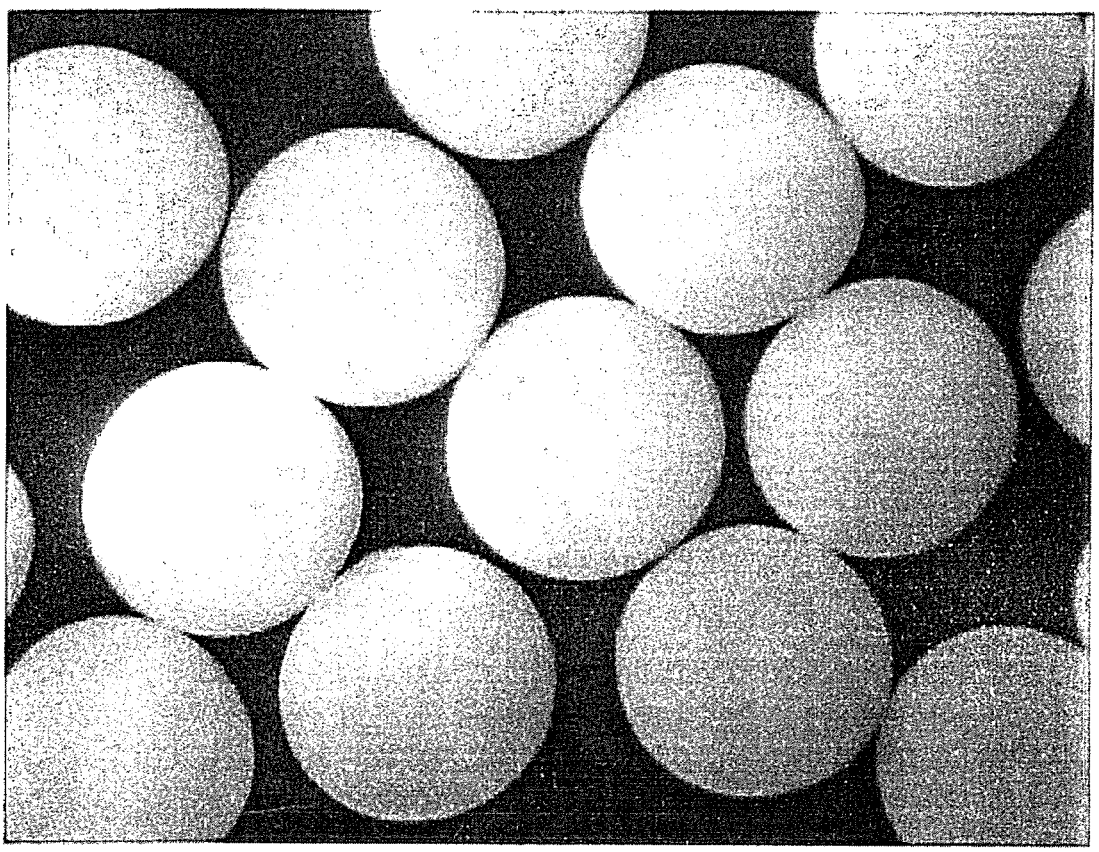
Figure 3B:
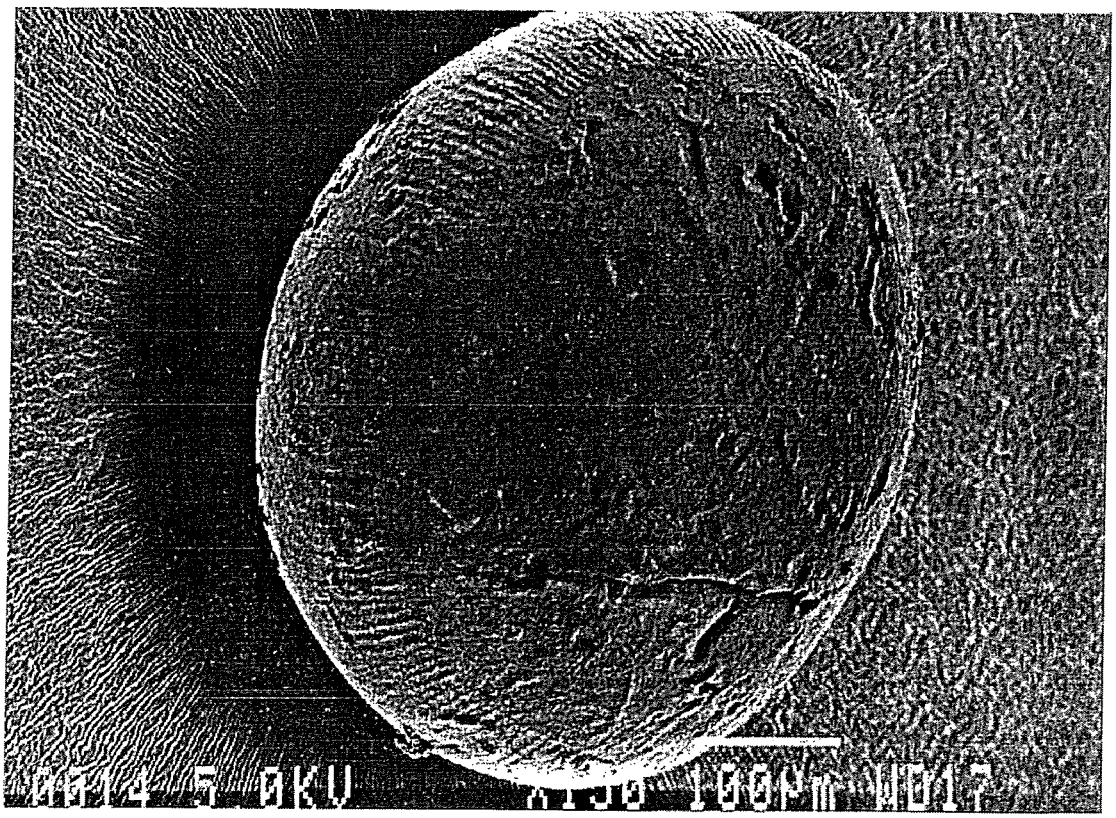
FIG. 3B is a scanning election microscope (SEM) photograph of a particle surface and FIGS. 3C-3E are cross-sections of particles.
Figure 3C:
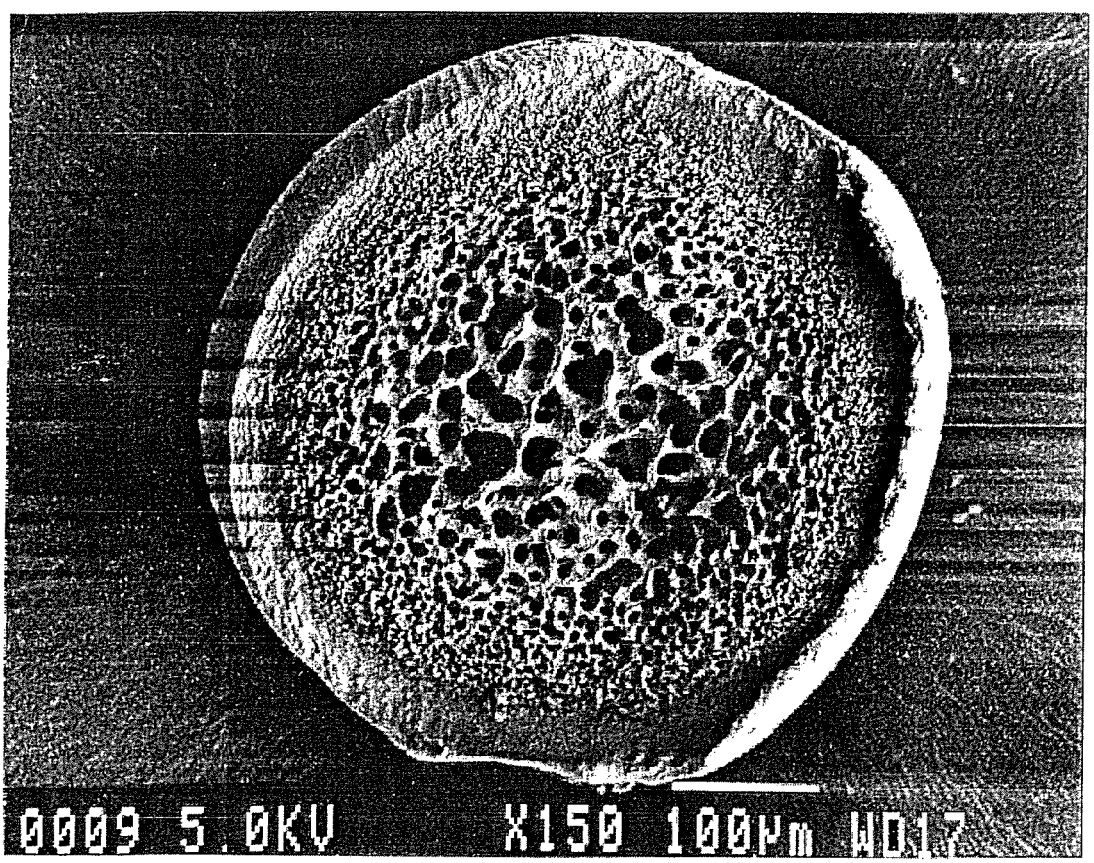
Figure 3C:
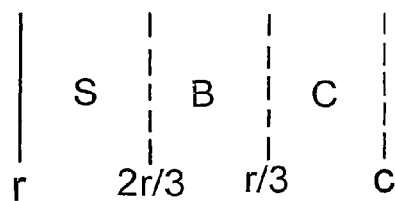
Figure 3D:
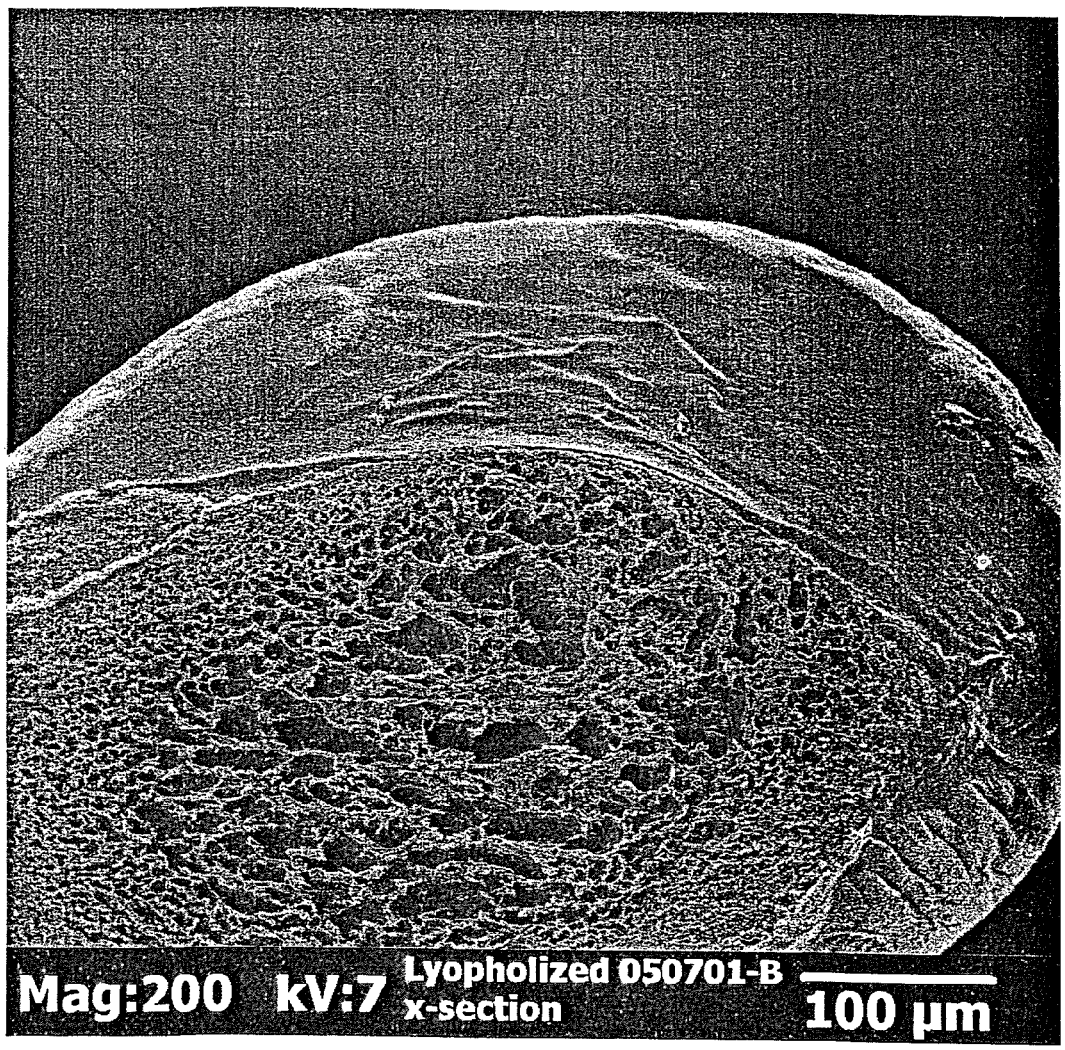
Figure 3E:
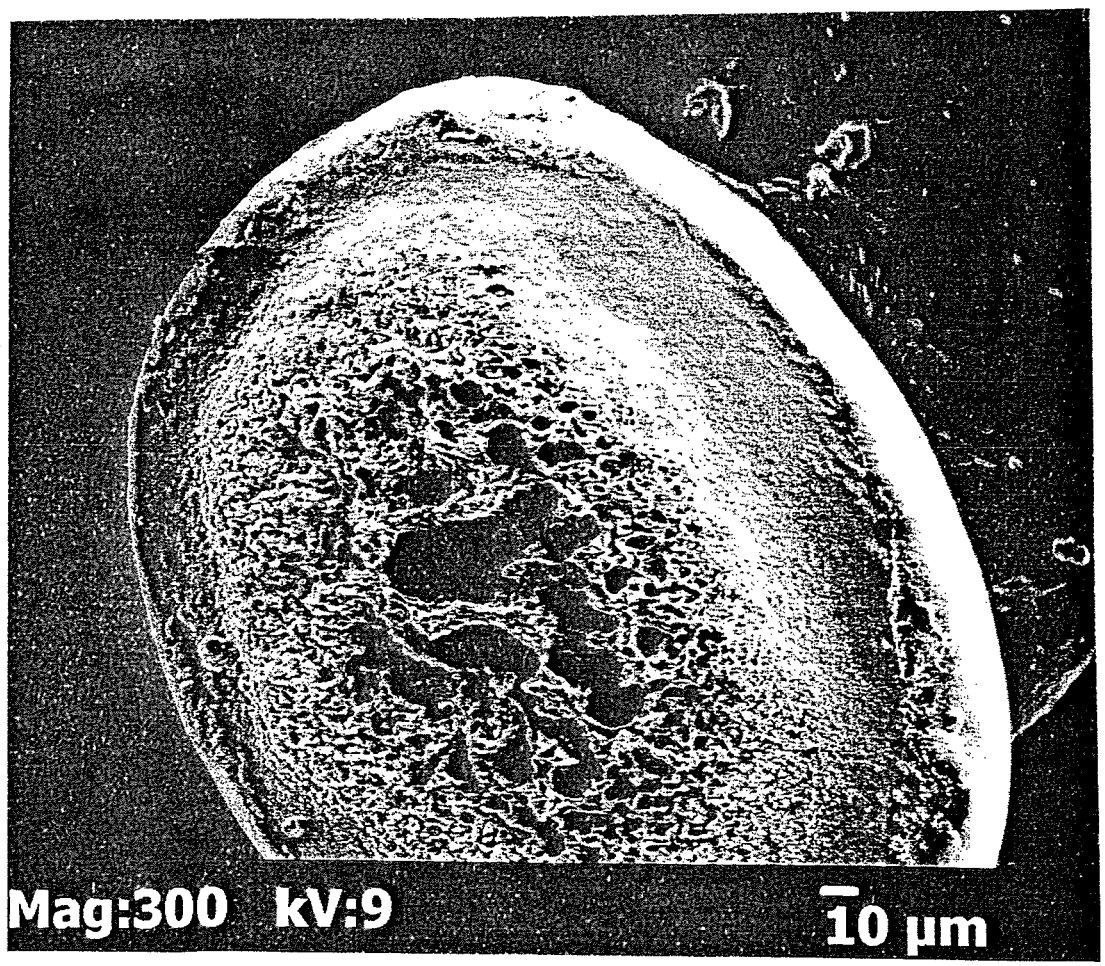

Referring to FIG. 3A, the particles have a substantially uniform shape and size. Referring to FIG. 3B, each particle has a well-defined outer spherical surface including relatively small, randomly located pores. Referring to FIGS. 3C-3E, SEM images of cross-sections through the particle, the body defines pores which provide metering of therapeutic agent release, as well as compressibility and other properties.

In embodiments, the small pore region near the periphery of the embolic particle is relatively stiff and incompressible, which enhances resistance to shear forces and abrasion. In addition, the variable pore size profile produces a symmetric compressibility and, it is believed, a compressibility profile such that the particles are relatively easily compressed from a maximum, at rest diameter to a smaller, compressed first diameter but compression to even smaller diameter requires substantially greater force. A variable compressibility profile is believed to be due to the presence of a relative weak, collapsible inter-pore wall structure in the center region where the pores are large, and a stiffer inter-pore wall structure near the surface of the particle, where the pores are more numerous and relatively small. The variable pore size profile also is believed to enhance elastic recovery after compression. The pore structure also influences the density of the embolic particles and the rate of therapeutic agent and body fluid uptake.

The particles can be delivered through a syringe or a catheter. The size of the lumen of the syringe or the catheter can be larger than the particle diameter to reduce compression of the particles during delivery, which can eject therapeutic agent from the particle prematurely. While compression can result in release of therapeutic agent, the metering region can retard substantial release under low compression force. In embodiments, the particles are compressed during delivery in order to use a delivery device that has a small diameter to reduce patient trauma or more accurately position the particles about a lesion. The carrier fluid in which the particles are suspended can include therapeutic agent so that upon recovery to normal diameter, the agent is drawn into the pores of the particle. For example, the particles can be delivered through a catheter having a lumen area that is smaller, e.g. 50% smaller or less, than the uncompressed cross-sectional area of the particles. The compression force is provided indirectly by increasing the pressure applied to the carrier fluid by pressing the syringe plunger. The particles are relatively easily compressed to diameters sufficient for delivery into the body. The robust, rigid surface region resists abrasion when the embolic particles contact hard surfaces such as syringe surfaces, hard plastic or metal stopcock surfaces, and the catheter lumen wall (e.g. Teflon) during delivery. Once in the body, the particles recover to original diameter for efficient transport in the carrier and body fluid stream. At the point of occlusion, the particles can again compress as they aggregate in an occlusion region. The particles form a dense occluding mass. The compression in the body is limited and the number of embolic particles needed to occlude a given diameter may be reduced. The particles can also be delivered directly into a tissue mass where reexpansion to a larger diameter firmy lodges the particle into the tissue.

In embodiments, the particles have a diameter in the range of 1 cm or less, e.g., 5 mm to 1 mm or less, e.g., about 1200 microns or less, and about 10 microns or more, e.g. about 400 microns or more and the pores are about 50 or 35 to 0.01 micron. Preferably, the particles are classified in size ranges of about 500-700 microns, about 700-900 microns, or about 900-1200 microns. The particles have a mean diameter in approximately the middle of the range and variance of about 20% or less, e.g. 15% or 10% or less.

Referring specifically to FIG. 3C, the particles can be considered to include a center region, C, from the center of the particle to a radius of about r/3, a body region, B, from about r/3 to about 2 r/3 and a surface region, S, from 2 r/3 to r. The regions can be characterized by the relative size of the pores and the number of pores of given sizes. In embodiments, the center region has a greater number of relatively large pores than the body region and the surface region. The large pores are in the range of about 20 micron or more, e.g. 30 micron or more, or in the range of about 20 to 35 micron. The body region has a greater number of intermediate size pores than the surface region. The intermediate size pores are in the range of about 5 to 18 micron. In embodiments, the regions may also have different densities, with the density of the surface region being greater than the density of the body region, and the density of the body region being greater than the density of the center region.

The size of the pores in each of the regions can also be characterized by a distribution. In embodiments, the predominant pore size(s) in the center region being greater than the predominant pore size(s) in the body region and the predominant pore size(s) in the body region is greater than the predominant pore size(s) in the surface region. In embodiments, in the predominant pore size in the center region is 20 micron or more, e.g. 30 microns or more, or in the range of about 20 to 35 microns. The predominant pore size in the body region is about 18 micron or less, e.g. about 15 micron or less, or in the range of about 18 to 2 micron. The pores in the surface region are preferably predominantly less than about 1 micron, e.g. about 0.1 to 0.01 micron.

In embodiments, the predominant pore size in the body region is about 50 to 70% of the pore size in the center region and the pore size in the surface region is about 10% or less, e.g. about 2% of the pore size in the body region. The size of the pores on the outer surface of the particle is predominantly in the range of about 1 micron or less, e.g. about 0.1 or 0.01 micron. In embodiments, the surface and/or surface region is substantially free of pores having a diameter larger than about 10 micron or larger than about 1 micron. In embodiments, the predominant pore size is in the region 0.8 or 0.9 r to r is about 1 micron or less, e.g. 0.5 to 0.1 micron or less. The region from the center of the particle to 0.8 or 0.9 r has pores of about 10 micron or greater and/or has a predominant pore size of about 2 to 35 micron. In embodiments, the predominant pore size in the region 0.8 or 0.9 r to r is about 5% or less, e.g. 1% or 0.3% or less than the predominant pore size in the region from the center to 0.9 r. the largest pores in the particles can have a size in the range of 1% or 5% or 10% or more of the particle diameter.

The size of the pores can be measured by viewing a cross-section as in FIG. 3C. For irregularly shaped pores, the maximum visible cross-section is used. The predominant pore size(s) can be found by measuring the size of the visible pores and plotting the number of pores as a function of size. The predominant pore size(s) are the sizes that are about the maximum in the distribution. In FIG. 3C, the SEM was taken on wet particles including absorbed saline, which were frozen in liquid nitrogen and sectioned. (FIG. 3B was taken prior to sectioning.) In FIGS. 3D and 3E, the particle was freeze-dried prior to sectioning and SEM analysis.

The density of the particles is such that they are readily suspended in the carrier fluid such as a mixture of saline and contrast solution and remain suspended during delivery. In embodiments, the density is in about 1.1-1.4 g/cm$^3$. For suspension in a saline-contrast solution, the density is about 1.2-1.3 g/cm$^3$. The sphericity after compression in a catheter to about 50% or more of their cross-sectional area is about 0.90 or 0.95 or greater. In embodiments, the particles can be manually compressed, essentially flattened, while wet to less than 50% of original diameter and then, upon exposure to fluid, regain a sphericity of about 0.9 or more. The carrier fluid can be a pharmaceutically acceptable carrier such as saline or contrast agent or therapeutic agent or a combination of these carriers. The particles or composition can be sterilized.

Manufacture

Figure 4A:
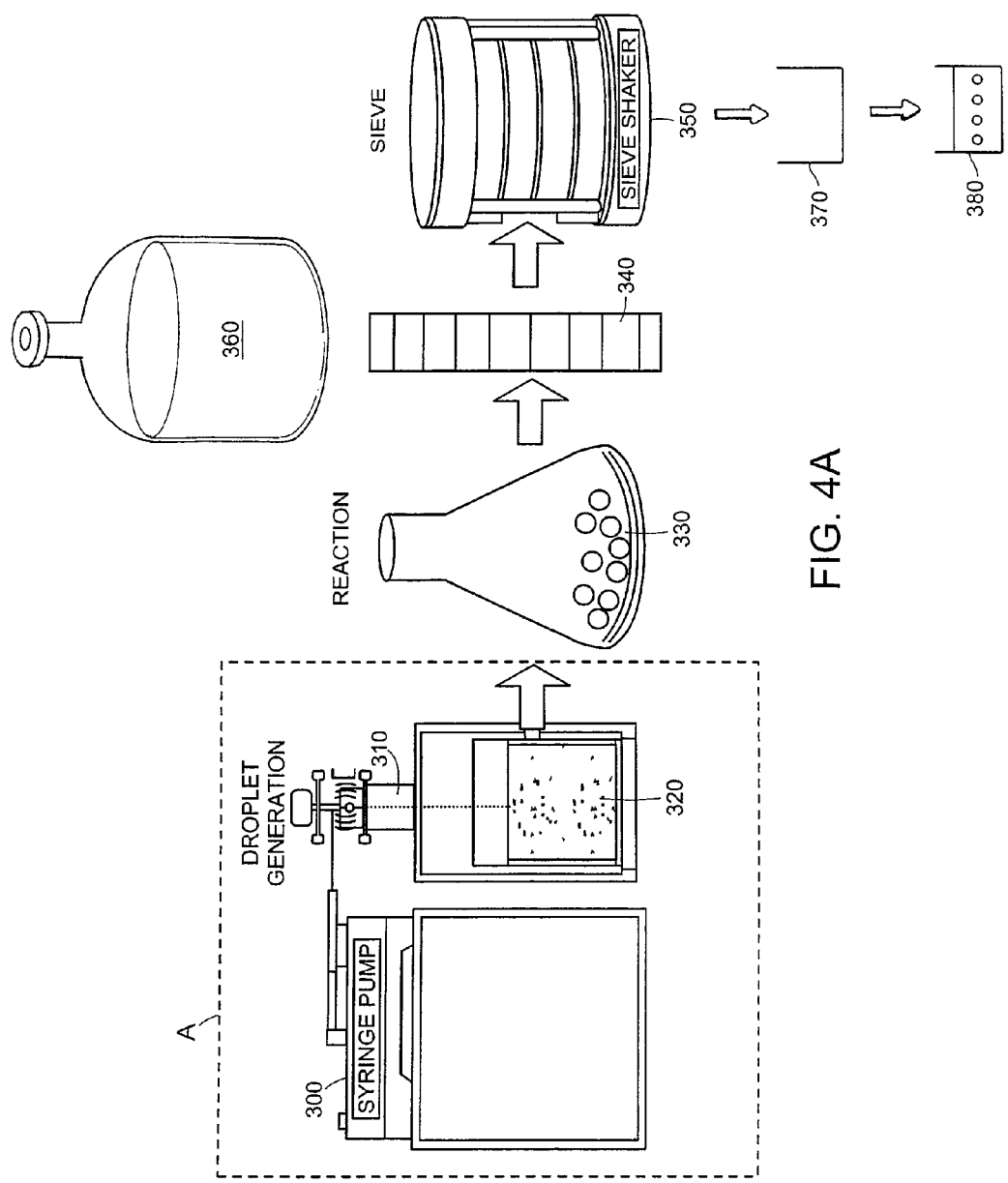

Referring to FIG. 4, a system for producing particles includes a flow controller 300, a drop generator 310, a gelling vessel 320, a reactor vessel 330, a gel dissolution chamber 340, a filter 350, a supply of therapeutic agent 360, a particle drying chamber 370, and a particle rehydrator vessel 380. The flow controller 300 delivers polymer solutions to a viscosity controller 305, which heats the solution to reduce viscosity prior to delivery to the drop generator 310. The drop generator 310 forms and directs drops into a gelling vessel 320, where drops are stabilized by gel formation. The gel-stabilized drops are transferred from the gelling vessel 320 to reactor vessel 330 where the polymer in the gel-stabilized drops are reacted forming precursor particles. The precursor particles are transferred to a gel dissolution chamber 340, where the gel is dissolved. The particles are then filtered in a filter 350 to remove debris, sterilized, and packaged as a composition including the particles. As will be discussed below, the therapeutic agent can be incorporated into the particles at various stages. In the embodiment illustrated, after filtering, the particles can be dried in a chamber 370, e.g. under vacuum (e.g., by lyophilization) with or without heat application or air dried with or without heat, e.g., at room temperature. The dried particles are then rehydrated in a vessel 380 which includes therapeutic agent. In the rehydration process, the therapeutic agent is drawn into the particles through the pore structure. The particles can then be packed in a solution of therapeutic agent. The particles can be mixed with saline or contrast agent at the time of administration.

A base polymer and a gelling precursor are dissolved in water and mixed. The mixture is introduced to a high pressure pumping apparatus, such as a syringe pump (e.g., model PHD4400, Harvard Apparatus, Holliston, Mass.). Examples of base polymers include polyvinyl alcohol, polyacrylic acid, polymethacrylic acid, poly vinyl sulfonate, carboxymethyl cellulose, hydroxyethyl cellulose, substituted cellulose, polyacrylamide, polyethylene glycol, polyamides, polyureas, polyurethanes, polyester, polyethers, polystyrene, polysaccharide, polylactic acid, polyethylene, polymethylmethacrylate and copolymers or mixtures thereof. A preferred polymer is polyvinyl alcohol. The polyvinyl alcohol, in particular, is hydrolyzed in the range of 80 to 99%. The weight average molecular weight of the base polymer can be in the range of 9000 to 186,000, 85,000 to 146,000 or 89,000 to 98,000. Gelling precursors include, for example, alginates, alginate salts, xanthan gums, natural gum, agar, agarose, chitosan, carrageenan, fucoidan, furcellaran, laminaran, hypnea, eucheuma, gum arabic, gum ghatti, gum karaya, gum tragacanth, hyaluronic acid, locust beam gum, arabinogalactan, pectin, amylopectin, other water soluble polysaccharides and other ionically crosslinkable polymers. A particular gelling precursor is sodium alginate. A preferred sodium alginate is high guluronic acid, stem-derived alginate (e.g. about 50 or 60% or more guluronic acid with a low viscosity e.g. about 20 to 80 cps at 20° C.) which produces a high tensile, robust gel. High molecular weight PVA is dissolved in water by heating, typically above about 70° C., while alginates can be dissolved at room temperature. The PVA can be dissolved by mixing PVA and alginate together in a vessel which is heated to autoclave temperature (about 121° C.). Alternatively, the PVA can be disposed in water and heated and the alginate subsequently added at room temperature to avoid exposing the alginate to high temperature. Heat can also be applied by microwave application. For PVA/alginate, the mixture is typically about 7.5 to 8.5%, e.g. about 8% by weight PVA and about 1.5 to 2.5%, e.g. about 2%, by weight alginate.

Figure 4B:
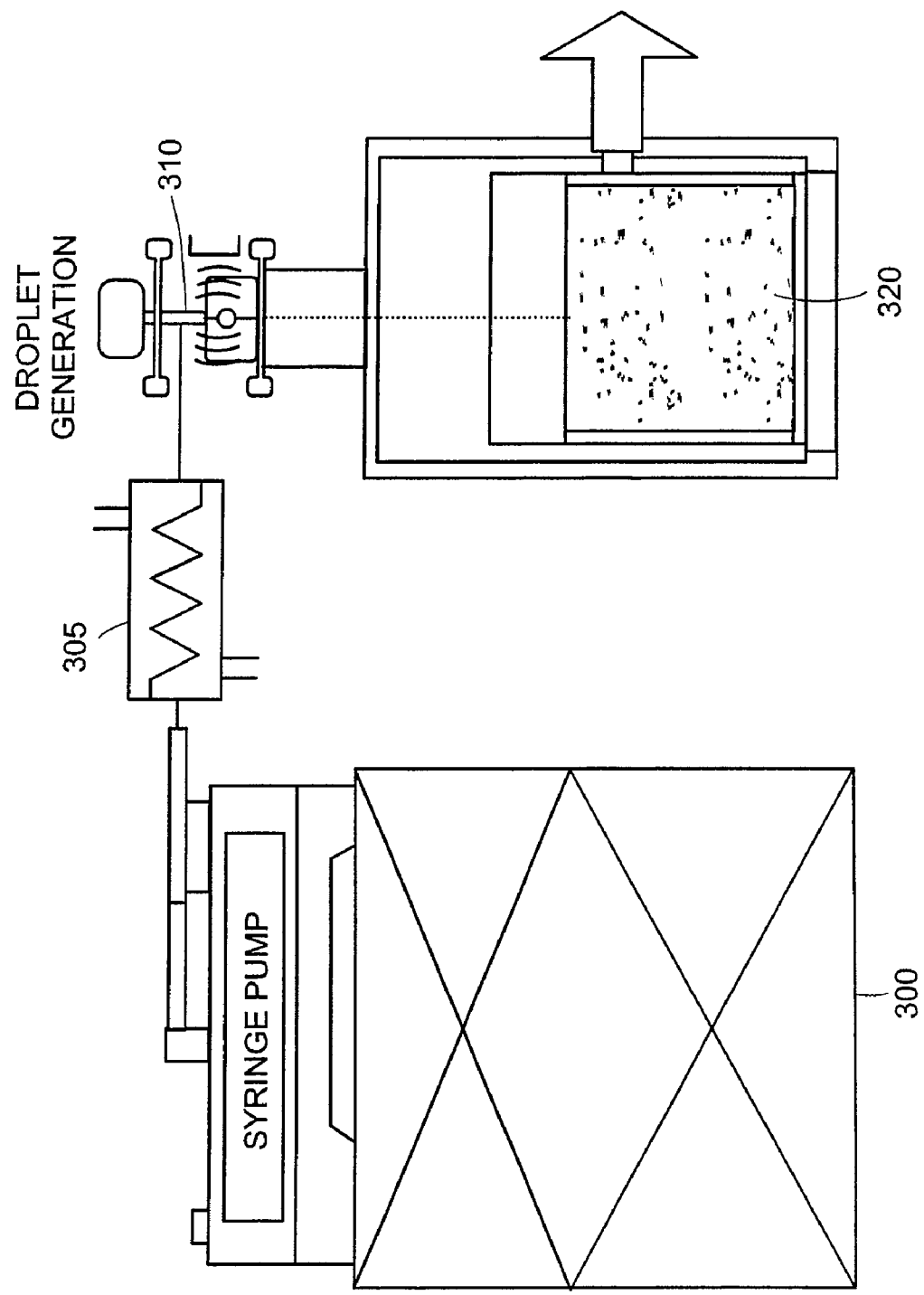
FIG. 4B is an enlarged schematic of region A in FIG. 4A.

Referring to FIG. 4B, the viscosity controller 305 is a heat exchanger circulating water at a predetermined temperature about the flow tubing between the pump and drop generator. The mixture of base polymer and gelling precursor flows into the viscosity controller 305, where the mixture is heated so that its viscosity is lowered to a level for efficient formation of very small drops. For a high molecular weight PVA/alginate solution, the temperature of the circulating water is less than about 75° C. and more than about 60° C., for example, 65° C. which maintains the mixture at a viscosity of 90-200 centipoise. For spherical particles, the viscosity of the drops is maintained so they are captured in the gelling vessel without splintering or cojoining which can create irregular, fiberous particles. In other embodiments, the flow controller and/or the drop generator can be placed in a temperature-controlled chamber, e.g. an oven, or a heat tape wrap, to maintain a desired viscosity.

The drop generator 310 generates substantially spherical drops of predetermined diameter by forcing a stream of the mixture of base polymer and gelling precursor through a nozzle which is subject to a periodic disturbance to break up the jet stream into drops. The jet stream can be broken into drops by vibratory action generated for example, by an electrostatic or piezoelectric element. The drop size is controlled by controlling the flow rate, viscosity, amplitude, and frequency at which the element is driven. Lower flow rates and higher frequencies produce smaller drops. A suitable electrostatic drop generator 310 is available from NISCO Engineering, model NISCO Encapsulation unit VAR D, Zurich, Switzerland. In embodiments, the frequency is in the range of about 0.1 to 0.8 kHz. The flow rate through the droplet generator is in the range of about 1 to 12 mL per minute. The drop generator can include charging the drops after formation such that mutual repulsion between drops prevents drop aggregation as they travel from the generator to the gelling vessels. Charging may be achieved by, e.g. an electrostatic charging device such as a charged ring positioned downstream of the nozzle.

Drops of the base polymer and gelling precursor mixture are captured in the gelling vessel 320. The gelling vessel 320 contains a gelling agent which interacts with the gelling precursor to stabilize drops by forming a stable gel. Suitable gelling agents include, for example, a divalent cation such as alkali metal salt, alkaline earth metal salt or a transition metal salt that can ionically crosslink with the gelling agent. An inorganic salt, for example, a calcium, barium, zinc or magnesium salt can be used as a gelling agent. In embodiments, particularly those using an alginate gelling precursor, a suitable gelling agent is calcium chloride. The calcium cations have an affinity for carboxylic groups in the gelling precursor. The cations complex with carboxylic groups in the gelling precursor resulting in encapsulation of the base polymer in a matrix of gelling precursor.

Figure 5:
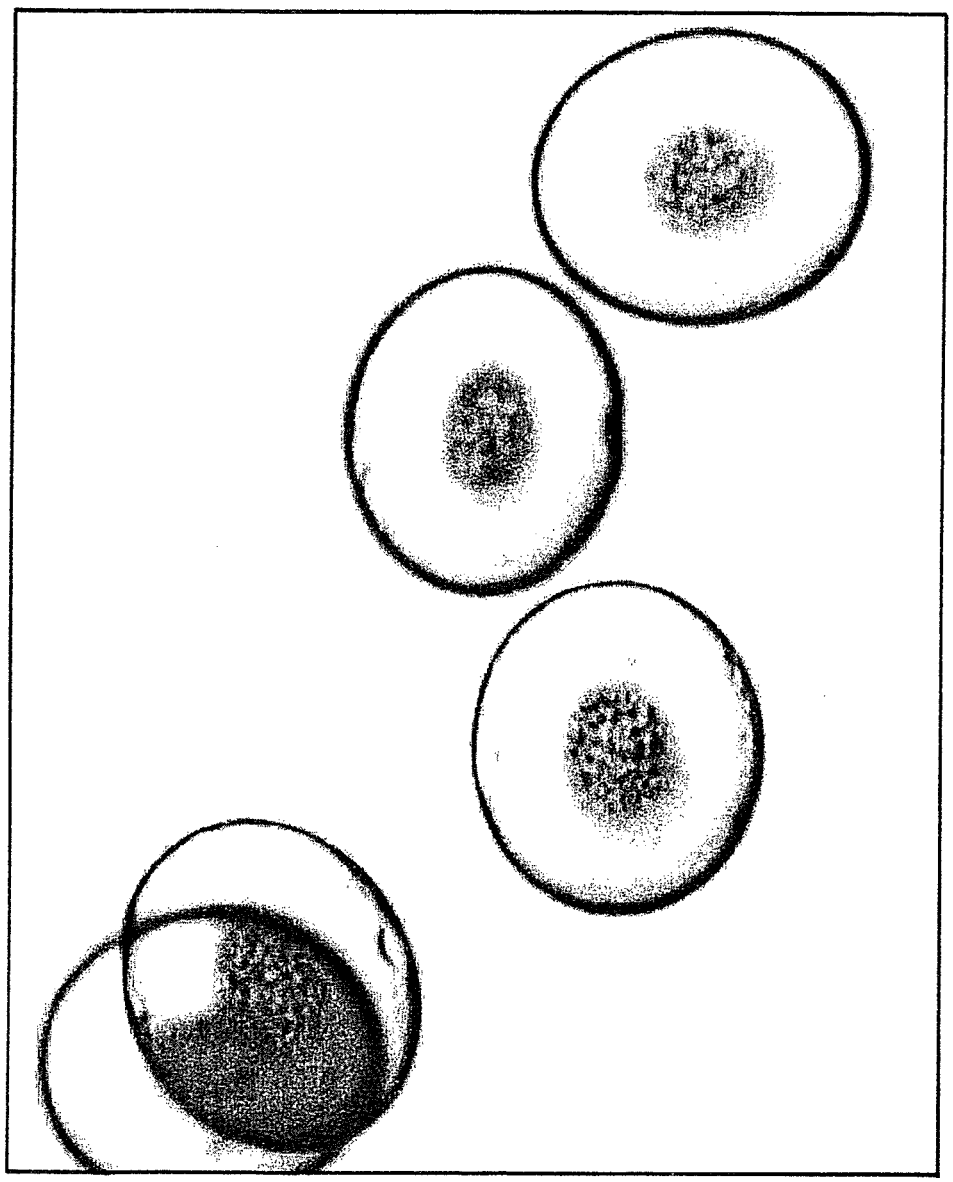
FIG. 5 is a photograph of gel-stabilized drops.
Figure 6:
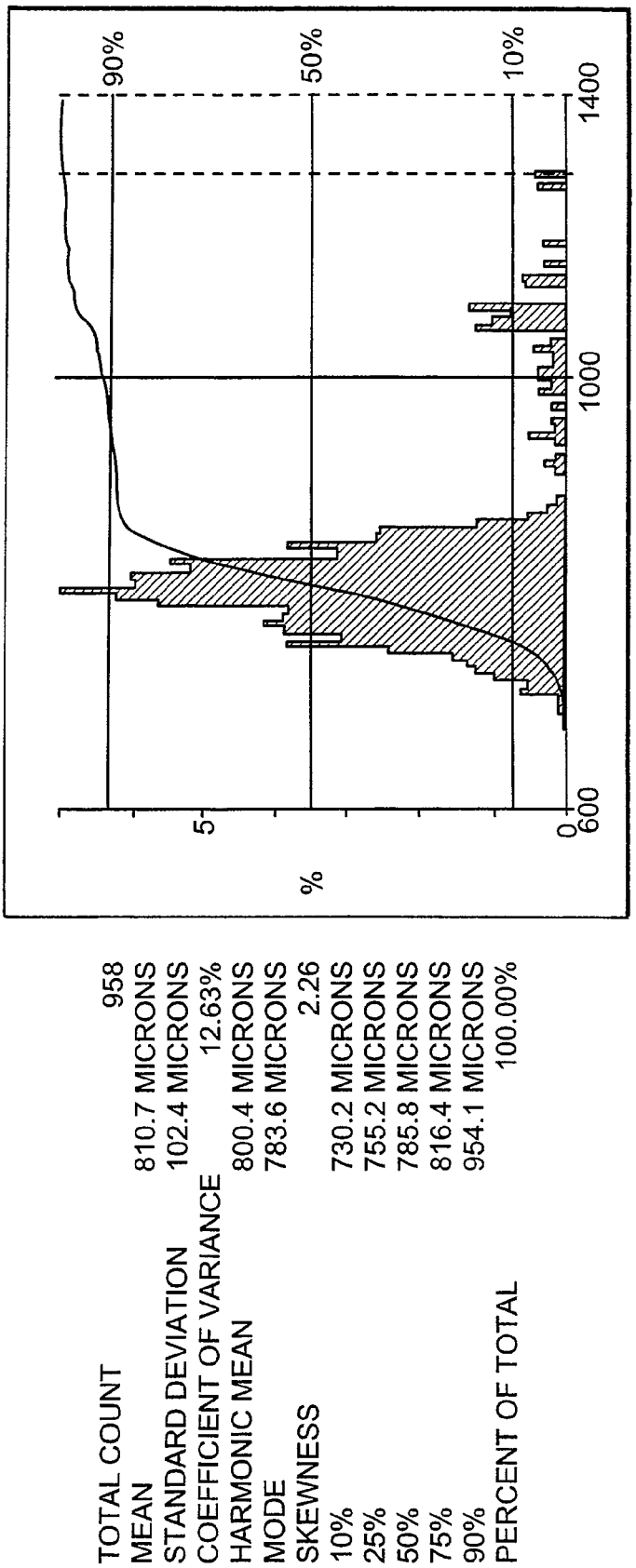
FIG. 6 is a graph of particles in uniformity.

Referring to FIG. 5, a photo-image of the gelled particles, the gelling agent is in an amount selected in accordance with the desired properties of the particles. A pore structure in the center of the particle forms in the gelling stage. The concentration of the gelling agent can control void formation in the embolic particle, thereby controlling the porosity gradient in the embolic particle. Adding non-gelling ions, for example, sodium ions, to the gelling solution can limit the porosity gradient, resulting in a more uniform intermediate porosity throughout the particle. In this manner the thickness and pore profile of the metering region can be controlled. In embodiments, the gelling agent is, for example, 0.01-10 weight percent, 1-5 weight percent or 2 weight percent in deionized water.

Following drop stabilization, the gelling solution is decanted from the solid drops and the stabilized drops are transferred to the reactor vessel 330. In the reactor vessel 330, the stabilized drops are reacted to produce precursor particles. The reactor vessel includes an agent that chemically reacts with the base polymer, e.g. to cause crosslinking between polymer chains and/or within a polymer chain. The agent diffuses into the stabilized drops from the surface of the particle in a gradient which, it is believed, provides more crosslinking near the surface of the stabilized drop compared to the body and center of the drop. Reaction is greatest at the surface of the drop, providing a stiff, abrasion resistant exterior. For polyvinyl alcohol, for example, the vessel 330 includes aldehydes, such as formaldehyde, glyoxal, benzaldehyde, aterephthalaldehyde, succinaldehyde and glutaraldehyde for the acetalization of polyvinyl alcohol. The vessel 330 also includes an acid, for example, strong acids such as sulfuric acid, hydrochloric acid, nitric acid and weak acids such as acetic acid, formic acid and phosphoric acid. In embodiments, the reaction is primarily a 1,3 acetalization:

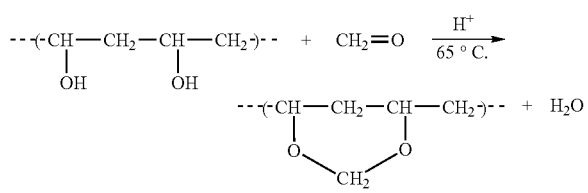

This intra-chain acetalization reaction can be carried out with relatively low probability of inter-chain crosslinking as described in John G. Pritchard "Poly(Vinyl Alcohol) Basic Properties And Uses (Polymer Monograph, vol. 4) (see p. 93-97), Gordon and Breach, Science Publishers LTD., London, 1970, the entire contents of which is hereby incorporated by reference. Some OH groups along a polymer chain may remain unconverted since the reaction proceeds in a random fashion and there will be left over OH groups that do not react with adjacent groups.

Adjusting the amount of aldehyde and acid used, reaction time and reaction temperature can control the degree of acetalization. In embodiments, the reaction time is e.g., 5 minutes to 1 hour, 10 to 40 minutes or 20 minutes. The reaction temperature can be 25° C. to 150° C. or 75° C. to 130° C. or 65° C. The reactor vessel is placed in a water bath fitted with a orbital motion mixer. The crosslinked precursor particles are washed several times with deionized water to neutralize the particles and remove any residual acidic solution.

The precursor particles are transferred to the dissolution chamber 340 to remove the gelling precursor, e.g. by an ion exchange reaction. In embodiments, sodium alginate is removed by ion exchange with a solution of sodium hexa-metaphosphate (EM Science). The solution can include, for example, ethylenediaminetetraacetic acid (EDTA), citric acid, other acids and phosphates. The concentration of the sodium hexa-metaphosphate can be, for example, 1-20 weight %, 1-10 weight % or 5 weight % in deionized water. Residual gelling precursor, for example, sodium alginate, can be determined by an assay for detection of uronic acids in, for example, alginates containing mannuronic and guluronic acid residues. Residual alginate, for example, may be present in the range of about 20-35% by weight prior to rinsing and in the range of about 0.01-0.5% or 0.1-0.3% or 0.18% in the particles after rinsing for 30 minutes in water at about 23° C.

The particles are filtered through filter 350 to remove residual debris. Particles of 500 to 700 microns are filtered through a sieve of 710 microns and then a sieve of 300 microns. Particles of 700 to 900 microns are filtered through a sieve of 1000 microns and then a sieve of 500 microns. Particles of 900 to 1200 microns are filtered through a sieve of 1180 microns and then a sieve of 710 microns.

The filtered particles are sterilized by a low temperature technique such as e-beam irradiation, and packaged, typically about 1 to 5 ml of particles in about 5 to 10 ml saline. In embodiments, electron beam irradiation can be used to pharmaceutically sterilize the particles to reduce bioburden. In e-beam sterilization, an electron beam is accelerated using magnetic and electric fields, and focused into a beam of energy. This resultant beam can be scanned by means of an electromagnet to produce a "curtain" of accelerated electrons. The accelerated electron beam penetrates the collection of embolic particles to confer upon them electrons which destroy bacteria and mold to sterilize and reduce the bioburden in the embolic particles. Electron beam sterilization can be carried out by sterilization vendors such as Titan Scan, Lima, Ohio.

The therapeutic agent can be incorporated in the particle at various stages. As discussed above, the agent may be added to the particle after particle formation. For example, the particle can be dried and rehydrated with the therapeutic agent or a solution including the therapeutic agent. Alternatively, the therapeutic agent can be added during particle formation. For example, the agent can be mixed with PVA and alginate upstream of droplet formation or after droplet formation in the gelling vessel, reaction vessel, or dissolution chamber or in a separate step after any of these stages. The particles may also be used to deliver therapeutic agent at the stabilized drop stage without cross-linking the base polymer or at the precursor particle stage with crosslinked base polymer with or without removing the gelling precursor or gelling agent. Alternatively, the therapeutic agent can be provided only to the surface and/or metering region, e.g., by coating particle, without including substantial amounts of agent in the interior portions of the particle, e.g., the reservoir region.

The particles can be coated to include high concentration of therapeutic agent on their surface. The agent on the surface can release an initial dosage of agent while agent in the body of the particle provides a prolonged dosage over the extended period of time. The agent on the surface can be the same or different from the agent in the body of the particle. The agent on the surface can be applied by exposing the particle to a high concentration solution of the agent. The agent coated particle can include another coating over the surface the therapeutic agent, e.g., a degradable polymer which erodes when the particle is administered or meters drug out flow from the surface, e.g., by providing a porous membrane. The coating can delay an initial burst of drug release. The coating can be applied by dipping or spraying the particle. The erodable polymer could be a polysaccharide, such as an alginate. Suitable material for alginate coatings are described in Edwards-Levy *Biomaterials* 1999, November 20 (21) 2069-84; *J. Microencapsol.* 1999 May-June 16(3); 291-301; and Takka et al. *J. Microencapsol.* 1999 May-June 16(3), 275-90. Other erodable coatings include water soluable polymers such as polyvinyl alcohol, e.g., that has not been cross-linked. Other coatings include biodegradeable poly DL-lactide-poly ethylene glycol (PELA) discussed in Zhou et al. *J. Control Release* 2001 July 10; 75; (1-2):27-36 or gelatin as discussed in Huang et al. *Int. J. Pharm* 1995 May 10 182(1):93-100. Other coatings include hydrogels such as polyacrylic acid, haluronic acid, gelatin, or carboxymethyl cellulose. Other coatings include polyethylene glycols (PEG), chitosan, polyesters such as polycaprolactones, and poly(de-lactic coglycolic acid (PLGA). Suitable coatings of these types are discussed in *J. Control Release*, vol. 78, 1-3, 17 Jan. 2002, pp. 15-24. The coatings can include therapeutic agent or be substantially free of therapeutic agent. The therapeutic agent in the coating can be the same or different as an agent on a surface layer of the particle and/or within the particle. A polymer coating, e.g. an erodable coating, can be applied to the particle surface in cases where a high concentration of drug has not been applied to the particle surface. The fluoroscopic visibility of the particle can be enhanced by incorporating a highly radiopaque material such as a metal, e.g. tantalum or platinum into the polymer matrix of the particle or the coating The particles can be modified by chemical or physical modifications that affect attachment and/or release of the therapeutic agent, the visibility of the particles, or their shape. For example, the polymer of the particle can be modified by graft polymerization to, for example, provide a reactive side chain. A therapeutic agent is attached covelantly or ionically to the reactive moiety of the graft polymer. A polymer that is grafted to the particle can be further polymerized to influence polymer chain length to create a molecular level morphology or vary hydrophobicity. Suitable graft polymers include polymers with carboxylic acid, anhydride, or aceto-acetyl groups which can be grafted to, e.g. PVA side groups modified to provide acrylic acids. Graft polymerization is discussed in *Biomaterials*, 2002 February 23 (3) 863-71 and "Polyvinyl Alcohol Developments," Ed. C. A. Finch, John Whiley, 1992 (see especially sections 6.2.3 and 7.3.1). Suitable graft polymers also include peptides that include cell binding domains. Examples are discussed in Hubbell, *Biomacromolecules*, 2002, vol. 3, 710-23. Species capable of cell membrane penetrations e.g. polyluecine oligomer can be attached to the particle to enhance cell attachment. Targeting ligands such as galactose can be introduced onto the surface of a particle. Galactose attachment onto polymers is discussed in *Biotechnology Bioengineering*, 2002 April 5 (78) 1-10. The grafted segment can be provided with reactive moieties such as amines, carboxylic acids or thiols to which therapeutic agent can be attached. The moieties can be used to modify the hydrophobic/hydrophilic and catonic/anionic nature of the particle surface. An example of a polymer that can be grafted is poly(vinyl alcohol)-graft-poly(lactic-co-glycolic acid) to produce brush-like branched polyesters for enhancing protein release, as discussed in Frauke-Pistel et al. *J. Control Release* 2001 May 18; 73(1):7-20. Particle charged and hydrophobicity can be modified by grafting. For example, a negatively charged hydrophilic backbone poly (2-sulfobutyl vinyl alcohol)-g-poly(lactide-co-glycolide) is described in Jung et al. *J. Control Release* 2000 July 3; 67(2-3):157-69.

The polymer of the particle can also be modified by, e.g. block copolymerization to provide reactive moieties for graft polymerization and/or for direct therapeutic agent attachment. The polymer can also be modified to provide reactive groups at specific sites. For example, hydroxyl groups of PVA can be modified to provide more reactive sites, such as e.g. amines, carboxylic acids, or thiols.

Release kinetics can also be modified by controlling crosslinking. Techniques for crosslinking PVA and controlling release kinetics are discussed in Kim et al. *Pharmaceutical Research*, vol. 9, No. 1 (1992); *Cosmetic and Pharm. App. For Polymers*, August 1990 p. 709-14; and *Polymer Mater. Sci. Eng.* (1990) vol. 63, p. 64-7. Crosslinking is also described in A. R. Bachtsi and C. Kiparissides *Journal of Microencapsulation*, 1995, vol. 12 part 1, p. 23-35; Tobata et al. *J. Control Release vol.* 50, part 1-3, p. 123-133; and Orenti et al., *Arch. Pharm* (Weinheim) 2000 December: 333 (12), 421-4 and Sappimath et al., *J. Biomat. Sci. Polym.* Ed. 2000j 11(i); 27-43.

The shape of the particles can be modified by physical deformation followed by crosslinking as described in U.S. Ser. No. 10/116,330 filed Apr. 14, 2002, the entire contents of which is incorporated herein by reference. The particles can be coated on or incorporated into other medical devices, such as implantable devices including stents, embolization coils, arterial filters, artificial heart valves, catheters, and balloons such as angioplasty balloons. Other medical delivery includes wound dressings.

Therapeutic Agents and Use

Therapeutic agents include materials that are biologically active to treat physiological condition. The agent can be active in release from the particle to tissue or active as it resides in the particle and is exposed to tissue or body fluid in communication with the particle.

The term "therapeutic agent" includes one or more "therapeutic agents" or "drugs". The terms "therapeutic agents" and "drugs" are used interchangeably and include pharmaceutically active compounds, nucleic acids with and without carrier vectors such as lipids, compacting agents (such as histones), virus (such as adenovirus, adeno-associated virus, retrovirus, lentivirus and a-virus), polymers, hyaluronic acid, gene therapies, proteins, cells, stem cells and the like, or combinations thereof, with or without targeting sequences.

Specific examples of therapeutic agents include, for example, pharmaceutically active compounds, proteins, cells, stem cells, oligonucleotides, ribozymes, antisense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a noninfectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/anti-proliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, dephalosporins, aminoglycosides, and nitrofurantoin; anesthetic agents such as lidocaine, bupivacaine, and ropivacaine; nitrix oxide (NO) donors such as lisidomine, molsidomine, L-argine, NO-protein adducts, NO-carbohydrate adducts, polymeric or oligomeric NO adducts; anti-coagulants such as D-Phe-Pro-Arg chloromethyl ketone, an RGD peptide-containing compound, heparine, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Any modifications are routinely made by one skilled in the art.

Useful polynucleotide sequences include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; growth factors; cell cycle inhibitors including CDK inhibitors, anti-restenosis agents, including p15, p16, p18, p19, p21, p27, p53, p57, Rb, nFkB and E2F decoys, thymidine kinase ("TK) and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Therapeutic agents include one or more of the following therapeutic agents: cells, stem cells, virus, protein, drug, enzymes, or combinations thereof.

Organs and tissues that may be treated include any mammalian tissue or organ, whether injected in vivo or ex vivo. Non-limiting examples include heart, lung, brain, liver, skeletal muscle, smooth muscle, kidney, bladder, intestines, stomach, pancreas, ovary, prostate, eye, tumors, cartilage and bone.

Other examples of therapeutic agents include the following.

Immunologic species such as antigens captured from specific cell lines (e.g. cancerous) can be absorbed/adsorbed or attached to surface of a particle, which can then be injected at the targeted cell mass, tissue or organ, e.g. a cancer site, to begin an immunologic reaction/cascade/response. Examples include HuRx, and DCVax from Northwest BioTherapeutics Inc., Bothell, Wash. An antigen or genetically engineered molecule can be used. For example, anti-EGF receptor antibodies which help lengthen the time chemotherapy can be used as a treatment for colorectal cancer can be used. Examples include Cetuximab from ImClone Systems, New York, N.Y. Antibodies or receptors, genetically engineered or not, can also be used. Monoclonal antibodies to cells of blood vessels interact in the angiogenesis cascade, which is important for the growth of tumors can be used.

Radioactive molecules for radiopacity and/or treatment for cancer may be absorbed/adsorbed or attached to the surface of PVA particulates. Examples include radioactive materials such as iodine (131), gold or yttrium.

Proteins required for signaling pathways may be absorbed/adsorbed or attached to the surface of the particulate including antibodies, antigens, monoclonal antibodies, proteins found on cancer cells, proteins found on diseased cells in any system, proteins found on normal, nondiseased state cells in any system, or others. Signaling pathways of interest include pathways for cell regeneration, for cell death, for angiogenesis, for cell growth, for chronic heart failure, for cell differentiation or others. Suitable proteins include platelet derived growth factor BB as described in Bourke, 2002 *Society for Biomaterials* 28$^{th}$ *Annual Meeting Transactions*, page 144.

Another particular therapeutic agent is vascular endothelial growth factor (VEGF) for enhancing endothelialization as described in *J. Control Release,* 2001, May 14, 14:72(1-3): 101-13.

Complete whole cells, pieces of cells, genetically engineered cells or cells made of components of more than one organism may be attached to the surface of the particulate. Treatment includes diabetes or any disease caused by the cells of that organ lacking in producing a specific hormone/protein/organic molecule, cancer or Alzheimer's disease or diseases caused by the cells producing an incorrect product that is not in their function to create.

Antimicrobial coatings could coat the surface of the PVA particulate to aid in lessening infection/immunologic response to the presence of these products in the body. Coatings include the use of zinc, silver, iodine, triclosan and/or ciprofloxacin in a resin/polymer such as polyurethane.

Antigrowth drugs for cancer treatment may be absorbed/adsorbed or attached to the surface of the particle. Examples include Herceptin and Gleevec from Genetech and Novartis respectively. Small molecule chemotherapy drugs for targeted cancer treatment. Examples include, Ethiodol, Doxorubicin, Cisplatin and Mitomycin-C.

Particular therapeutic agents for treatment of liver tumors include agents used in chemoembolization, such as carboplatin, cisplatin, doxorobicin, mytomycinc and ethiodol, as discussed in Jean-Francois Geschwind, Dimitri Artemov et al., *Journal of Vascular Interventional Radiology* (2000) 11:1245-1255; Dheeraj Rajan, Michael Soulen et al, *Journal of Vascular Interventional Radiology* (2001) 12:187-193; and Leung, Goin and Sickies et al., *Journal of Vascular Interventional Radiology* (2001) 12:321-326. A particular tumor-toxic agent e.g. for liver treatment is paclitaxol, available from Bristol-Meyers Squib, New York, N.Y.

Particular therapeutic agents useful for treatment of uterine fibroid tumors include nonsteriodal anti-inflammatory medication, oral contraceptives, progestins, and gonadotrophin-releasing hormone agonists which may cause fibroid tumors to shrink as described in Levy et al., *Journal of Women's Imaging* 2(4):168-175, 2000. Other therapeutic agents for uterine fibroid shrinkage include lupron, as discussed in Lipman, *Appl. Radiol.* 29(7):15-20, 2000.

Therapeutic agent may also include agents which bind to specific biological environments. The agents could, for example be placed on the exterior of the particle to make the particle targetable. The particles can be used for oral or topical administration as well as percutaneous administration. The particles can be used in chemoembolization in which drug is injected to a site and the particles are used to embolize the vasculature. The particles can include the same or a different agent or no agent. The particles can be used in combination with hydrogel based aneurysm embolization systems as described in Cruise et al., 2002, *Society for Biomaterials* 28th *Annual Meeting Transactions,* page 203. Other applications include drug delivery for treatment of anyeurums, coronary artery disease, restenosis and benign prostatic hyperplasia, e.g. in combination with medical devices such as stents.

EXAMPLE

Particles are manufactured from an aqueous solution containing 8 weight % of polyvinyl alcohol, 99+% hydrolyzed, average $M_w$ 89,000-120,000 (ALDRICH) and 2 weight % of gelling precursor, sodium alginate, PRONOVA UPLVG, (FMC BioPolymer, Princeton, N.J.) in deionized water and the mixture is heated to about 121° C. The solution has a viscosity of about 310 centipoise at room temperature and a viscosity of about 160 cps at 65° C. Using a syringe pump (Harvard Apparatus), the mixture is fed to drop generator (Nisco Engineering). Drops are directed into a gelling vessel containing 2 weight % of calcium chloride in deionized water and stirred with a stirring bar. The calcium chloride solution is decanted within about three minutes to avoid substantial leaching of the polyvinyl alcohol from the drops into the solution. The drops are added to the reaction vessel containing a solution of 4% by weight of formaldehyde (37 wt % in methanol) and 20% by weight sulfuric acid (95-98% concentrated). The reaction solution is stirred at 65° C. for 20 minutes. Precursor particles are rinsed with deionized water (3×300 mL) to remove residual acidic solution. The sodium alginate is substantially removed by soaking the precursor particles in a solution of 5 weight % of sodium hexa-meta-phosphate in deionized water for 0.5 hour. The solution is rinsed in deionized water to remove residual phosphate and alginate. The particles are filtered by sieving, as discussed above, placed in saline (USP 0.9% NaCl) and followed by irradiation sterilization.

Particles were produced at the nozzle diameters, nozzle frequencies and flow rates (amplitude about 80% of maximum) described in Table I.

TABLE 1

| Bead Size (microns) | Nozzle Diameter (microns) | Frequency (kHz) | Flow Rate (mL/min) | Density (g/mL) | Sphericity | Suspendability (minutes) |
|---|---|---|---|---|---|---|
| 500-700 | 150 | 0.45 | 4 | — | 0.92 | 3 |
| 700-900 | 200 | 0.21 | 5 | 1.265 | 0.94 | 5 |
| 900-1200 | 300 | 0.22 | 10 | — | 0.95 | 6 |

Suspendability is measured at room temperature by mixing a solution of 2 ml of particles in 5 ml of saline and 5 ml of contrast solution (Omnipaque 300, Nycomed, Buckinghamshire, UK) and observing the time for about 50% of the particles to enter suspension, i.e. not sink to the bottom or float to the top of a container (about 10 ml, 25 mm dia vial). Suspendability provides a practical measure of how long the particles will remain suspended in use. (Omnipaque is an aqueous solution of Tohexol, N.N.-Bis (2,3-dihydroxypropyl)-T-[N-(2,3-dihydroxypropyl)-acetamide]-2,4,6-trilodo-isophthalamide; Omnipaque 300 contains 647 mg of iohexol equivalent to 300 mg of organic iodine per ml. The specific gravity of 1.349 of 37° C. and an absolute viscosity 11.8 cp at 20° C.) The particles remain in suspension for about 2-3 minutes.

Particle size uniformity and sphericity is measured using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures particles in an image in the form of a fiber, rod or sphere.

Sphericity computation and other statistical definitions are in Appendix A, attached, which is a page from the RapidVUE operating manual.

Referring to FIG. 5, particle size uniformity is illustrated for particles 700-900 micron. The x-axis is the particle diameter. The y-axis is the volume normalized percentage of particle at each particle size. The total volume of particles detected is computed and the volume of the particles at each diameter is divided by the total volume. The embolic particles have distribution of particle sizes with variance of less than about ±15%.

The particles can be dried by lypholization at −20 to 20° C. and a pressure of about 75 mtorr for about 30 to 70 hours. The dried particles can be rehydrated by exposure to liquid. Exposure to contrast solution indicates that rehydration achieves entry of fluid throughout the particle.

The entire contents of all publications and patent documents referenced herein is incorporated herein by reference.

Still further enhancements are in the following claims.

What is claimed is:

1. A composition, comprising:
substantially spherical particles having a diameter of from about 10 microns to about 1 cm, the particles including a first region with pores having a first predominant pore size and a second region surrounding the first region and with pores having a second predominant pore size, the first predominant pore size being larger than the second predominant pore size, and the particles comprising cross-linked polyvinyl alcohol,
wherein the second region is about r to 2r/3, and r is a radius of the particles.

2. The composition of claim 1, wherein the first predominant pore size is about 20 micron or more.

3. The composition of claim 1, wherein the first predominant pore size is about 30 micron or more.

4. The composition of claim 1, further comprising a third region from about 2r/3 to r/3 and including pores having a third predominant pore size, wherein the third predominant pore size is larger than the second predominant pore size and smaller than the first predominant pore size.

5. The composition of claim 4, wherein the first region is from about r/3 to C, and C is a center of the particles.

6. The composition of claim 5, wherein the first predominant pore size is about 20 micron or more.

7. The composition of claim 6, wherein the third predominant pore size is from about 2 to about 18 microns.

8. The composition of claim 1, wherein the second region is substantially free of pores greater than about 5 micron.

9. The composition of claim 1, wherein the predominant pore size generally, progressively increases from surface to the center of the particle.

10. The composition of claim 1, wherein the predominant pore size on the particle surface is about 1 micron or less.

11. The composition of claim 1, wherein the second predominant pore size is about 1 micron or less.

12. The composition of claim 11, wherein the second predominant pore size is about 0.1 micron or less.

13. The composition of claim 11, wherein, interior of the second region, the particles have a predominant pore size in the range of about 2 to 35 microns.

14. The composition of claim 12, wherein the first region is from about C to r/3 and the first predominant pore size is about 20 to 35 micron, and C is the center of particles, and r is a radius of the particles.

15. The composition of claim 13, wherein the particles have a third region from r/3 to (2r)/3 and including pores having a third predominant pore size, in which the third predominant pore size is about 2 to 18 micron.

16. The composition of claim 1, wherein the second region is from about (2r)/3 to the surface of the particles, the second predominant pore size is about 10% or less than the first predominant pore size, and r is a radius of the particles.

17. The composition of claim 1, further comprising a carrier fluid having a density of about 1.1 to about 1.4 g/cm$^3$.

18. The composition of claim 1, wherein each of the particles has a sphericity of about 90% or more.

19. The composition of claim 1, wherein the particles have a size uniformity of about +15% or more.

20. The composition of claim 1, wherein the particles include about 1% or less polysaccharide.

21. The composition of claim 20, wherein the polysaccharide is alginate.

22. The composition of claim 21, wherein the alginate has a guluronic acid content of about 60% or greater.

23. The composition of claim 1, wherein the particles are substantially free of collagen.

24. The composition of claim 1, wherein the polyvinyl alcohol is predominantly intrachain 1,3-diols acetalized.

25. The composition of claim 1, further comprising a pharmaceutically acceptable medium in which particles are suspended.

* * * * *

UNITED STATES PATENT AND TRADEMARK OFFICE
CERTIFICATE OF CORRECTION

| | | |
|---|---|---|
| PATENT NO. | : 7,951,402 B2 | Page 1 of 1 |
| APPLICATION NO. | : 12/235978 | |
| DATED | : May 31, 2011 | |
| INVENTOR(S) | : Janel L. Lanphere et al. | |

It is certified that error appears in the above-identified patent and that said Letters Patent is hereby corrected as shown below:

Cover Page, item (56), Other Publications, in the 6th Citation: before "pp. 1-6, May 20, 2003.", delete "ablaeling.htm," and insert --alabeling.htm,--.

Column 16, Claim 19, Line 32: delete "+15%" and insert --±15%--.

Signed and Sealed this
Twelfth Day of July, 2011

David J. Kappos
*Director of the United States Patent and Trademark Office*